US012752079B2

(12) United States Patent
Bleier

(10) Patent No.: US 12,752,079 B2
(45) Date of Patent: Oct. 6, 2026

(54) SUBMUCOSAL DRUG DELIVERY APPARATUSES, SYSTEMS, AND METHODS

(71) Applicant: Massachusetts Eye and Ear Infirmary, Boston, MA (US)

(72) Inventor: Benjamin S. Bleier, Weston, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 685 days.

(21) Appl. No.: 16/968,093

(22) PCT Filed: Feb. 8, 2019

(86) PCT No.: PCT/US2019/017178
§ 371 (c)(1),
(2) Date: Aug. 6, 2020

(87) PCT Pub. No.: WO2019/157259
PCT Pub. Date: Aug. 15, 2019

(65) Prior Publication Data
US 2021/0023295 A1 Jan. 28, 2021

Related U.S. Application Data

(60) Provisional application No. 62/627,878, filed on Feb. 8, 2018.

(51) Int. Cl.
*A61M 25/00* (2006.01)
*A61B 1/00* (2006.01)
(Continued)

(52) U.S. Cl.
CPC .... *A61M 25/0082* (2013.01); *A61M 25/0041* (2013.01); *A61M 25/0084* (2013.01);
(Continued)

(58) Field of Classification Search
CPC .............. A61M 5/145; A61M 25/0041; A61M 25/0082; A61M 25/0084; A61M 29/02;
(Continued)

(56) References Cited

U.S. PATENT DOCUMENTS 5,735,817 A * 4/1998 Shantha .................. A61F 7/123 604/113
6,293,922 B1 9/2001 Haase et al.
(Continued)

FOREIGN PATENT DOCUMENTS

CN 107898540 A 4/2018
EP 2532300 12/2012
(Continued)

OTHER PUBLICATIONS

Office Action in European Appln. No. 19750916.9, dated Apr. 3, 2023, 4 pages.
(Continued)

*Primary Examiner* — Kami A Bosworth
*Assistant Examiner* — Avery Smale
(74) *Attorney, Agent, or Firm* — Fish & Richardson P.C.

(57) ABSTRACT

The present disclosure relates to apparatuses and methods of depot delivery of therapeutic agents. The apparatuses provide a drug delivery device including a catheter component having a stem portion and a branch portion. The catheter component includes a pre-defined bend such that the branch portion is angled with respect to the stem portion at an obtuse angle. The branch portion includes a dissecting head and at least one delivery port. The drug delivery device includes a dilation balloon positioned on the branch portion between the pre-defined bend and the dissecting head, a drug delivery reservoir fluidly coupled to the at least one delivery port and a handle portion.

24 Claims, 26 Drawing Sheets

(51) Int. Cl.
*A61B 1/05* (2006.01)
*A61B 17/24* (2006.01)
*A61M 5/145* (2006.01)

(52) U.S. Cl.
CPC ............. *A61B 1/00071* (2013.01); *A61B 1/05* (2013.01); *A61B 17/24* (2013.01); *A61M 5/145* (2013.01); *A61M 2210/0618* (2013.01); *A61M 2210/0681* (2013.01)

(58) Field of Classification Search
CPC ...... A61M 2210/0681; A61M 25/0067; A61M 25/0068; A61M 25/0074; A61M 25/10; A61M 2025/1081; A61M 2025/1093; A61M 2025/0089; A61M 2025/009; A61M 2025/0091; A61B 1/00071; A61B 1/05; A61B 17/24; A61B 2017/320048; A61B 17/3478; A61B 2017/320044; A61B 2017/320052
See application file for complete search history.

(56) References Cited

U.S. PATENT DOCUMENTS

| | | | | |
|---|---|---|---|---|
| 6,478,775 | B1 * | 11/2002 | Galt | A61B 17/00491 604/266 |
| 8,673,338 | B2 | 3/2014 | Bleier | |
| 8,945,600 | B2 | 2/2015 | Bleier | |
| 9,084,756 | B2 | 7/2015 | Bleier | |
| 9,439,852 | B2 | 9/2016 | Bleier | |
| 9,517,200 | B2 | 12/2016 | Bleier | |
| 2001/0018584 | A1 | 8/2001 | Bays | |
| 2005/0124977 | A1 | 6/2005 | Gonzalez et al. | |
| 2005/0182390 | A1 | 8/2005 | Shanley | |
| 2005/0240147 | A1 | 10/2005 | Makower et al. | |
| 2006/0004323 | A1 * | 1/2006 | Chang | A61F 2/186 604/28 |
| 2006/0106361 | A1 | 5/2006 | Muni et al. | |
| 2007/0255233 | A1 | 11/2007 | Haase | |
| 2009/0187098 | A1 * | 7/2009 | Makower | A61B 90/36 600/101 |
| 2010/0099946 | A1 * | 4/2010 | Jenkins | A61B 1/0014 606/199 |
| 2010/0174308 | A1 | 7/2010 | Chang et al. | |
| 2011/0166522 | A1 | 7/2011 | Haase et al. | |
| 2012/0239004 | A1 | 9/2012 | Wong | |
| 2013/0085472 | A1 | 4/2013 | Shaari | |
| 2013/0174849 | A1 | 7/2013 | Atkinson et al. | |
| 2014/0107427 | A1 * | 4/2014 | Chow | A61M 25/0108 600/249 |
| 2014/0213966 | A1 | 7/2014 | Ostapoff et al. | |
| 2014/0257237 | A1 | 9/2014 | Kamen et al. | |
| 2015/0011951 | A1 | 1/2015 | Hwang et al. | |
| 2015/0099934 | A1 * | 4/2015 | Sartore | A61M 16/0486 600/187 |
| 2015/0133851 | A1 | 5/2015 | Reif et al. | |
| 2015/0165176 | A1 | 6/2015 | Makower et al. | |
| 2015/0320972 | A1 | 11/2015 | Racz | |
| 2016/0193145 | A1 | 7/2016 | Bleier | |
| 2016/0367286 | A1 | 12/2016 | Drontle et al. | |
| 2017/0150984 | A1 | 6/2017 | Breen | |
| 2021/0077781 | A1 | 3/2021 | Cichocki, Jr. et al. | |
| 2021/0378947 | A1 | 12/2021 | Amiji et al. | |

FOREIGN PATENT DOCUMENTS

| | | |
|---|---|---|
| WO | WO 2006/079055 | 7/2006 |
| WO | WO 2016/160967 | 10/2016 |
| WO | WO 2017/017543 | 2/2017 |
| WO | WO 2020/149993 A1 | 7/2020 |
| WO | WO 2022/212288 | 10/2022 |

OTHER PUBLICATIONS

Bernal-Sprekelsen et al., "Closure of cerebrospinal fluid leaks prevents ascending bacterial meningitis," Rhinology, 2005, 43:277-281.
Bleier et al., "Antibiotic eluting chitosan glycerophosphate implant in the setting of acute bacterial sinusitis: a rabbit model," Am J Rhinol Allergy, 2010, 24:129-32.
Bleier et al., "Chitosan glycerophosphate-based semirigid dexamethasone eluting biodegradable stent," Am J Rhinol Allergy, 2009, 23:76-79.
Bleier et al., "Current management of juvenile nasopharyngeal angiofibroma: A tertiary center experience 1999-2007," Am J Rhinol Allergy, 2009, 23:328-330.
Bleier et al., "Laser-assisted cerebrospinal fluid leak repair: an animal model to test feasibility," Otolaryngol Head Neck Surg., 2007, 137:810-4.
Bleier et al., "Mucocele Rate Following Endoscopic Skull Base Reconstruction Using Vascularized Pedicled Flaps," Am J Rhinol Allergy, 2011, 25:186-7.
Bleier et al., "Permeabilization of the Blood-Brain Barrier via Mucosal Engrafting: Implications for Drug Delivery to the Brain," PLOS ONE, Apr. 2013, 8(4):e61694, 7 pages.
Bleier et al., "Temporospatial quantification of fluorescein-labeled sinonasal irrigation delivery," Int Forum Allergy Rhinol., 2011, 1:361-5.
Brookmeyer et al., "Forecasting the global burden of Alzheimer's disease," Alzheimer's & Dementia, 2007, 3:186-191.
Cardoso et al., "Looking at the blood-brain barrier: molecular anatomy and possible investigation approaches," Brain Res Rev., 2010, 64:328-363.
Chiu et al., "An anatomical study of the arteries of the anterior nasal septum," Otolaryngol. Head Neck Surg., 2006, 134(1):33-36.
Dhuria et al., "Intranasal delivery to the central nervous system: mechanisms and experimental considerations," J Pharm Sci., 2010, 99:1654-73.
Dietz et al., "Application of a blood-brain-barrier-penetrating form of GDNF in a mouse model for Parkinson's disease," Brain Res., 2006, 1082:61-6.
Extended European Search Report in European Appln. No. 19750916.9, dated Sep. 30, 2021, 6 pages.
Francardo et al., "Impact of the lesion procedure on the profiles of motor impairment and molecular responsiveness to L-DOPA in the 6-hydroxydopamine mouse model of Parkinson's disease," Neurobiol. Dis., 2011, 42:327-340.
Illum, "Is nose-to-brain transport of drugs in man a reality?" Journal of Pharmacy and Pharmacology, 2004, 56:3-17.
Illum, "Nasal drug delivery-possibilities, problems and solutions," J Control Release, 2003, 87:187-98.
Luppi et al., "Chitosan-based Hydrogels for Nasal Drug Delivery: from Inserts to Nanoparticles," Expert Opin. Drug Deliv., 2010, 7(7):811-828.
Merkus et al., "Can nasal drug delivery bypass the blood-brain barrier ?: Questioning the direct transport theory," Drugs R D., 2007, 8:133-44.
Modi et al., "Advances in the treatment of neurodegenerative disorders employing nanotechnology," Ann N Y Acad Sci., 2010, 1184:154-172.
Nance et al., "A dense poly(ethylene glycol) coating improves penetration of large polymeric nanoparticles within brain tissue," Sci Transl Med., 2012, 4:149ra119.
Ngwuluka et al., "Levodopa delivery systems: advancements in delivery of the gold standard, " Expert Opin Drug Deliv., 2010, 7:203-24.
PCT International Preliminary Report on Patentability in International Appln. No. PCT/US2019/017178, dated Aug. 20, 2020, 9 pages.
PCT International Search Report and Written Opinion in International Appln. No. PCT/US2019/017178, dated Apr. 30, 2019, 11 pages.
Ranganath et al., "Hydrogel Matrix Entrapping PLGA-Paclitaxel Microspheres: Drug Delivery with Near Zero-Order Release and Implantability Advantages for Malignant Brain Tumour Chemotherapy," Pharm Res., 2009, 26(9):2101-14.

(56) References Cited

OTHER PUBLICATIONS

Shoichet et al., "Cell delivery to the central nervous system," Adv Drug Deliv Rev., 2000, 42: 81-102.
Zhao et al., "Intranasal delivery of nerve growth factor to protect the central nervous system against acute cerebral infarction," Chin Med Sci J., 2004, 19:257-61.
International Search Report and Written Opinion in International Appln. No. PCT/US2022/022205, mailed on Jun. 22, 2022, 9 pages.
Huang and Reichardt, "Neurotrophins: roles in neuronal development and function," Annu Rev Neurosci., 2001, 24:677-736, 64 pages.
International Preliminary Report on Patentability in International Appln. No. PCT/US2022/022205, mailed Oct. 12, 2023, 7 pages.
Khorkova and Wahlestedt, "Oligonucleotide therapies for disorders of the nervous system," HHS Public Access Author Manuscript, doi: 10.1038/nbt.3784, published online Jul. 13, 2018, published in final edited form as: Nat Biotechnol., Mar. 2017, 35(3):249-263, 36 pages.
Modarresi et al., "Inhibition of natural antisense transcripts in vivo results in gene-specific transcriptional upregulation," Nat Biotechnol., Mar. 2012, 30(5):453-9.
Murer et al., "Brain-derived neurotrophic factor in the control human brain, and in Alzheimer's disease and Parkinson's disease," Prog Neurobiol., Jan. 2001, 63(1):71-124.
Padmakumar et al., "Minimally Invasive Nasal Depot (MIND) technique for direct BDNF AntagoNAT delivery to the brain," HHS Public Access Author Manuscript, doi: 10.1016/j.jconrel.2021.01.027, published online Mar. 10, 2022, published in final edited form as: J Control Release, Mar. 2021, 331:176-186, 33 pages.
Palasz et al., "BDNF as a Promising Therapeutic Agent in Parkinson's Disease," Int J Mol Sci., Feb. 2020, 21(3):1170, 23 pages.
Pawar et al., "Direct CNS delivery of proteins using thermosensitive liposome-in-gel carrier by heterotopic mucosal engrafting," PLoS One, Dec. 2018, 13(12):e0208122, 15 pages.
Extended European Search Report in European Appln. No. 22781976.0, mailed on Jan. 23, 2025, 10 pages.

* cited by examiner

SUBMUCOSAL DRUG DELIVERY APPARATUSES, SYSTEMS, AND METHODS

RELATED APPLICATIONS

The present application is a 371 US National Stage Entry of PCT/US2019/017178, filed on Feb. 8, 2019, which claims priority to U.S. Provisional Patent Application No. 62/627,878, filed Feb. 8, 2018, entitled, "SUBMUCOSAL DRUG DELIVERY APPARATUSES, SYSTEMS, AND METHODS," which application is incorporated herein by reference in its entirety.

TECHNICAL FIELD

The present application relates generally to the field of drug delivery.

BACKGROUND

Various neurological disorders can be treated through the delivery of drugs or therapeutic agents to the central nervous system. Biological defenses such as the blood brain-barrier prevent many therapeutic agents, such as proteins and oligonucleotides, from reaching the central nervous system, thereby inhibiting the efficacy of the therapeutic agents. Surgically implanted mucosal grafts allow therapeutic agents to be effectively delivered at high molecular weight to the central nervous systems; however, certain patients, such as infant and pediatric patients, are not well suited for surgical treatment.

Direct transnasal delivery (e.g., spaying) of therapeutic agents for diffusion through the olfactory mucosa is one non-surgical method for delivering therapeutic agents to patients not well suited for or surgery or for whom surgery is impractical or impossible. However, direct transnasal delivery has highly inefficient and variable drug distribution and drug residence time in view of the variation and limitations of available surface area for delivery to the olfactory through topical nasal applications.

SUMMARY

The inventor has discovered that the efficacy of non-invasive delivery of therapeutic agents to the central nervous system is greatly enhanced through controlled depot delivery directly to the submucosal space of the olfactory mucosa. The controlled depot delivery elutes drug over a prescribed period of time based on the polymer or carrier used. By dosing in the submucosal space, the barriers to diffusion to the olfactory nerves are minimized relative to transepithelial delivery and the drugs are thereby protected from multiple degradative enzymes present in nasal mucus.

Accordingly, various embodiments disclosed herein provide apparatuses, systems, and methods for a controlled depot delivery where a drug can be delivered directly to the submucosal space of the olfactory mucosa. The apparatuses create a precision controlled pocket in this space in a reproducible manner to standardize the volume of drug delivery. The apparatuses permit delivery of an array of drug carriers from solutions and thermosensitive polymers to solid formulations.

Various embodiments provide drug delivery devices for submucosal drug delivery. The drug delivery devices include a catheter component comprising a stem portion and a branch portion. The catheter component includes a pre-defined bend whereby the branch portion is angled with respect to the stem portion at an obtuse angle. The branch portion includes a dissecting head and at least one delivery port. The dilation balloon is positioned on the branch portion between the pre-defined bend and the dissecting head. The dilation balloon can advance from the outer sheath along the branch portion. Once the dilation balloon advances into position, the dilation balloon is configured to expand around at least a portion of a cylindrical wall of the branch portion. The drug delivery device includes a drug delivery reservoir fluidly coupled to the drug delivery port through the branch portion and through at least a portion of the stem portion. The drug delivery device includes a handle portion coupled to the stem portion.

The dilation balloon enables pocket formation to precise specifications through a small mucosal puncture, thereby preventing loss of drug through the mucosal puncture site and minimizing trauma that can occur to the mucosa over repeated injections.

In certain implementations, the drug delivery device includes an outer sheath positioned between the pre-defined bend and the dilation balloon.

In certain implementations, the branch portion is configured to retract into and extend from the outer sheath at the obtuse angle.

In certain implementations, at least a portion of the branch portion is configured to retract into and extend from the outer sheath at the obtuse angle.

In certain implementations, the dilation balloon is configured to retract into and extend from the outer sheath at the obtuse angle with the branch portion.

In some implementations, the devices also enable direct visualization of the pocket to enable precise pocket placement in the correct plane while minimizing the risk of injury or penetration of the overlying mucosa and prevent injury or penetration of the skull base. Accordingly, certain implementations comprise an onboard micro-endoscope device that enables direct visualization and pocket development during navigation of the narrow olfactory cleft by the drug delivery device. The endoscope is positioned adjacent to the pre-defined bend so as to have a field of view of the dissecting head and the plane above the dissecting head.

In some implementations, the endoscope comprises a camera.

In certain implementations, the dissecting head comprises a flattened disc geometry.

In certain implementations, the dissecting head comprises a beveled edge.

In certain implementations, the dissecting head comprises a cannula having a diameter in the range of 0.25 mm and 3 mm.

In certain implementations, the drug delivery device includes a pump communicably coupled to the drug delivery reservoir and configured to move a drug from the drug delivery reservoir to the at least one delivery port.

In certain implementations, the pump comprises a plunger assembly.

In certain implementations, the obtuse angle is in the range of 155-170 degrees.

In certain implementations, the branch portion has a length in the range of 10-20 cm.

In certain implementations, the balloon has length in the range of 1-4 cm.

In certain implementations, the balloon has a diameter in the range of 0.1-3 mm.

In certain implementations, the balloon is configured to dilate asymmetrically.

In certain implementations, the branch is configured to extend 2-3 cm pass the outer sheath.

In certain implementations, the branch portion extends upstream and downstream of the balloon portion such that the balloon is positioned between the dissecting head a section of the branch portion that is narrower than balloon in an inflated state, whereby the cross section of the entry to the depot upon retraction of the branch portion is narrower than the cross section of the depot.

In certain implementations, the reservoir contains a therapeutically effective amount of a drug for treating a central nervous system disorder. In certain implementations, the therapeutically effective amount of the drug from treating the central nervous system disorder comprises at least one of oligonucleotides and antibodies. In certain implementations, the therapeutically effective amount of the drug from treating the central nervous system disorder comprises at least one pharmaceutical agent with a molecular size of greater than 500 Da (e.g., greater than 600 Da, 700 Da, 800 Da, 900 Da, 1 kDa, 2 kDa, 3 kDa, 4 kDa, 5 kDa, 10 kDa, 20 kDa, 30 kDa, 70 kD, or 100 kD) or a net positive or net negative charge. In certain implementations, the therapeutically effective amount of the drug from treating the central nervous system disorder comprises at least one pharmaceutical agent that is a polar molecule. In certain implementations, the therapeutically effective amount of the drug comprises at least one pharmaceutical agent present in the composition that decreases unregulated or mis-regulated cell growth (e.g., reduces the rate of cancer cell growth), mediates or induces cancer cell death (e.g., necrosis or apoptosis), decreases protein misfolding and/or aggregation, mediates an increase or decrease in neurohormone or neurotransmitter production or turn-over, decreases loss of myelin, reduces neuronal cell death or neuronal loss, reduces loss of axons, mediates an increase or decrease in neurohormone or neurotransmitter receptor activity, mediates an increase or decrease in synaptic transmission between neurons, and mediates an increase or decrease in neuronal intracellular signaling pathways. In some compositions, the at least pharmaceutical agent is an analgesic.

In certain implementations, the therapeutically effective amount of the drug comprises at least one of a chemotherapeutic agent, L-DOPA, carbidopa, an anti-depressant agent, an anti-psychotic agent, donepezil, rivastigmine tartrate, galantamine, memantine, ISIS-SOD1, ISIS-SMN, ISIS-TTR, ELND005, β- or γ-sectretase inhibitors, neurotrophic peptides, nanoparticles, fusion proteins, and gene therapy vectors.

Non-limiting examples of chemotherapeutic agents include proteins (e.g., antibodies, antigen-binding fragments of antibodies, or conjugates or derivatives thereof), nucleic acids, lipids, or small molecules, or combinations thereof. Non-limiting examples of chemotherapeutic agents include: cyclophosphamide, mechlorethamine, chlorabucil, melphalan, daunorubicin, doxorubicin, epirubicin, idarubicin, mitoxantrone, valrubicin, paclitaxel, docetaxel, etoposide, teniposide, tafluposide, azacitidine, azathioprine, capecitabine, cytarabine, doxifluridine, fluorouracil, gemcitabine, mercaptopurine, methotrexate, tioguanine, bleomycin, carboplatin, cisplatin, oxaliplatin, all-trans retinoic acid, vinblastine, vincristine, vindesine, vinorelbine, and bevacizumab (or an antigen-binding fragment thereof). Additional examples of chemotherapeutic agents are known in the art.

Non-limiting examples of anti-depressant agents include: selective serotonin reuptake inhibitors (e.g., citalopram, escitalopram, fluoxetine, paroxetine, or sertraline), serotonin-norepinephrine reuptake inhibitors (e.g., desvenlafaxine, duloxetine, milnacipran, and venlafaxine), noradrenergic and specific serotonergic antidepressants (e.g., mianserin and mirtazapine), norephinephrine reuptake inhibitors (e.g., atomoxetine, mazindol, reboxetine, and viloxazine), norepinephrine-dopamine reuptake inhibitors (e.g., bupropion), selective serotonin reuptake enhancers (e.g., tianeptine), norephinephrine-dopamine disinhibitors (e.g., agomelatine), tricyclic antidepressants (e.g., amitriptyline, clomipramine, doxepin, imipramine, and trimipramine), secondary amine tricyclic depressants (e.g., desipramine, nortriptyline, and protripyline), monoamine oxidase inhbitors (e.g., isocarboxazid, moclobemide, phenelzine, selegiline, and tranylcypromine), buspirone, gepirone, nefazodone, tandospirone, trazodone, bupropion, benzodiazepines, amphetamine, methylphenidate, modafinil, lithium, carbamazepine, sodium valproate, and lamotrigine. Non-limiting examples of anti-psychotic agents include risperidone, olanzapine, and quetiapine.

In certain implementations, the dissecting head is configured to create an opening having a cross sectional area that is smaller than a cross sectional area of the dilation balloon when inflated.

Various implementations provide methods of drug delivery. The methods include inserting a catheter component of a drug delivery device into a submucosal tissue by penetrating the tissue via a dissecting head positioned at an end of a branch portion of the catheter component extending from a stem portion of the catheter component. The catheter component includes a pre-defined bend whereby the branch portion is angled with respect to the stem portion at an obtuse angle. The methods include creating a depot in the submucosal tissue by inflating a dilation balloon positioned on the branch portion between the pre-defined bend and the dissecting head to compress the submucosal tissue. The methods include deflating the dilation balloon. The methods include ejecting a drug through a delivery port in the dissecting head. The drug is pushed or pumped from a drug reservoir through the stem portion and the branch portion.

All combinations of the foregoing concepts and additional concepts discussed in greater detail below (provided such concepts are not mutually inconsistent) are part of the inventive subject matter disclosed herein. In particular, all combinations of claimed subject matter appearing at the end of this disclosure are part of the inventive subject matter disclosed herein. Terminology explicitly employed herein that also may appear in any disclosure incorporated by reference should be accorded a meaning most consistent with the particular concepts disclosed herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages will be apparent from the following detailed description, and from the claims.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

The features and advantages of the inventive concepts disclosed herein will become more apparent from the detailed description set forth below when taken in conjunction with the drawings.

DETAILED DESCRIPTION

Following below are more detailed descriptions of various concepts related to, and exemplary embodiments of, inventive systems, methods, and components related to optical fiber coupling systems.

Figure 1:
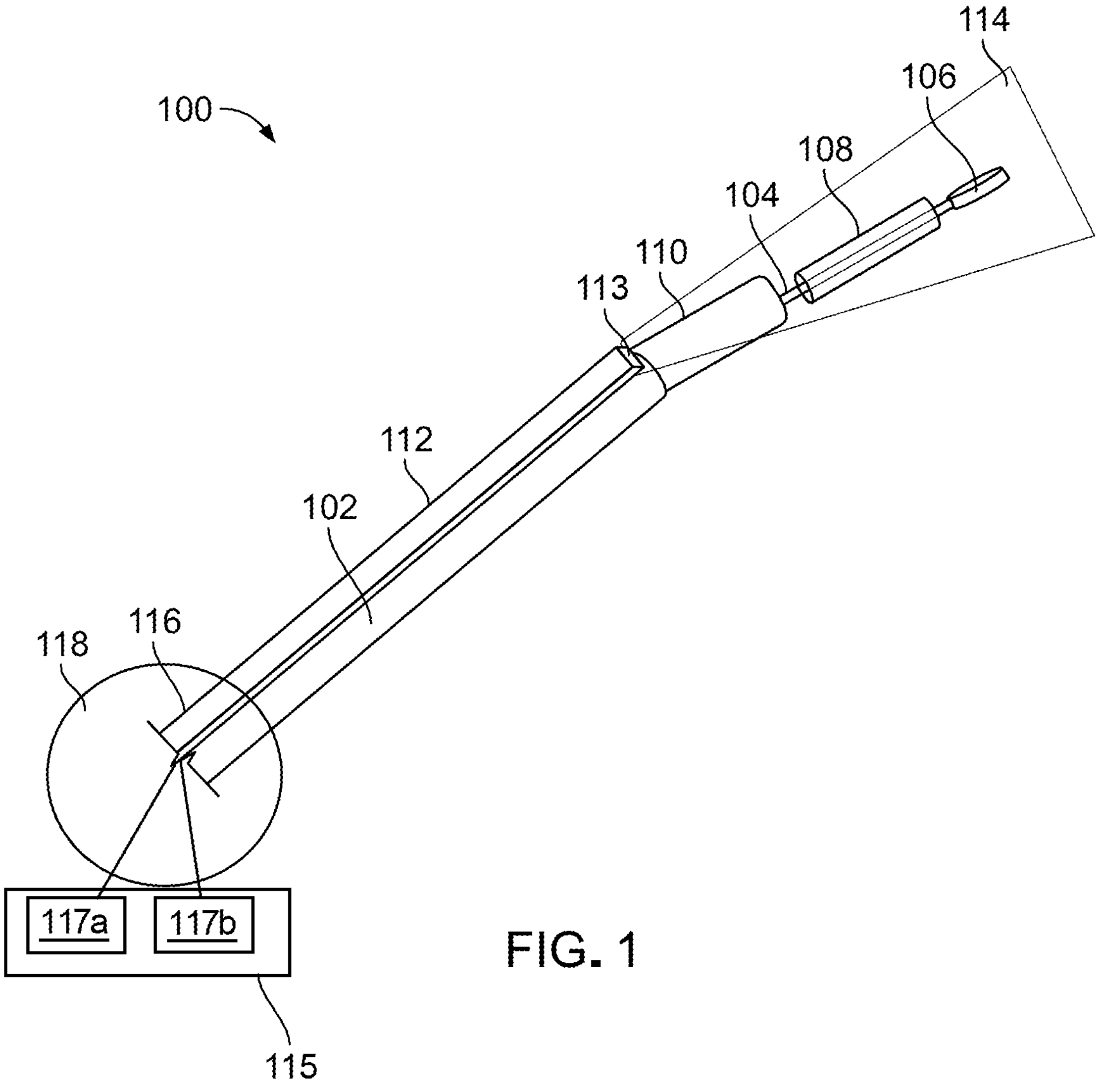
FIG. 1 shows a top perspective view of a drug delivery device as described herein.

FIG. 1 shows a top perspective view of a drug delivery device as described herein. A drug delivery device 100 is particularly suited for olfactory submucosal depot delivery of a drug or therapeutic agent. As described in further detail herein, the drug delivery device 100 allows a large standardized space to be created with a pinhole opening to enable a precise volume of a therapeutic agent to be deposited trans olfactory while substantially preventing the drug from leaking out of the submucosal space. The drug delivery device 100 includes a catheter component 100 having two portions, a stem portion 102 and a branch portion 104. The catheter component 100 includes a pre-defined bend about a point so that the branch portion 104 of the catheter component 100 is positioned at an angle with respect to the stem portion 102. In particular, the branch portion 104 is positioned at an obtuse angle with respect to the stem portion 102. In certain implementations, the branch portion 104 is angulated with respect to the stem portion 102 in the range of 155-170 degrees (i.e. the angle between the stem portion 102 and the branch portion 104). The catheter component 100 is composed out of surgical metal in certain implementations and has a rigidity that allows it to maintain the pre-defined angulated shape during insertion. The angulation of the branch portion 104 with respect to the stem portion 102 allows the drug delivery depot or space to be properly created in the olfactory mucosa while limiting or precluding intracranial penetration or penetration of the skull base. The angulation of the branch portion 104 with respect to the stem portion 102 allows the drug delivery depot to be created substantially parallel to the olfactory bulb in the submucosal space, for example in supramucoperichondrial or submucoperichondrial plane.

The catheter component 100 includes a dissecting head 106 positioned at the tip of the branch portion 104. The dissecting head 106 is on a leading edge of the branch portion 104 to create a pinhole opening through the olfactory mucosa tissue as the drug delivery device is advanced therein. The dissecting head 106 includes a flattened disc geometry (e.g., flat semi-circular) in certain implementations. The dissecting head 106 includes a tapered or beveled geometry in certain implementations. The dissecting head comprises a port coupled via a channel extending through the branch portion 104 and at least a portion of the stem portion 102. Accordingly, the dissecting head is configured as a cannula or a needle tip in certain implementations. The port provides a pathway for fluids to be delivered through the catheter component 100 to the depot created thereby. In certain implementations, the port is used to retrieve anatomical fluids. The port is connected to a reservoir 118 in certain implementations. The reservoir 118 can be positioned adjacent to and/or in a handle portion 116. The reservoir 118 is used to hold a drug or the therapeutic agent for delivery. The drug can be pumped from the reservoir 118 to the port via an actuator generating a change in pressure in the catheter component 100. The drug can include a liquid, a gel (e.g., thermosensitive gels), and/or a solid in accordance with certain implementations.

The catheter component 100 also includes a dilation balloon 108, positioned on the branch portion. The dilation balloon 108 is positioned between the pre-defined bend in the catheter component and the dissecting head 106. The dilation balloon 108 is configured to expand upon actuation. The actuation can be initiated via an actuator button positioned on or near the handle 116. In some implementations, the dilation balloon is fluidly coupled to a fluid source for increasing the volume of the balloon. Expansion of the dilation balloon creates the olfactory submucosal depot by compressing the tissue in the region. The dilation balloon 108 is positioned so that the dissecting head 106 is upstream of the dilation balloon 108 and at least a portion of the branch portion 104 is downstream of the dilation balloon 108. This configuration ensures that once the dilation balloon 108 is contracted back from the expanded state, before the branch portion is at least partially retracted, the pinhole opening created via the dissecting head 106 upon entry into submucosa space maintains its size (e.g. smaller than the depot and smaller than the expanded dilation balloon). In certain implementations, the dilation balloon 108 has a length in the range of 1-4 cm, an inflated diameter in the range of 0.1-3 mm. The dilation balloon 108 is symmetrical in certain implementations, but may also be configured asymmetrically in particular implementations. Maintaining the size of the opening smaller than the depot creates a bottleneck to limit the flow or exit of any delivered drug from the opening through which the dissecting head 106 created and is extracted. As discussed further herein, after the dilation balloon is contracted from its expanded state, the branch portion 104 is at least partially retracted from the depot or void created by the dilation balloon 108 and the drug or therapeutic agent is ejected through the port in the branch portion to reside in the depot for diffusion into the central nervous system. While the dilation balloon 108 is illustrated by way of example as cylindrical, the dilation balloon can be formed in a variety of different shapes or geometries to form various depot geometries and size, for example depending on the patient, dosage, and/or therapeutic agent or drug.

In certain implementations, the catheter component 100 also includes an outer sheath 110. The outer sheath 110 is positioned downstream of the bend in the catheter component 100. The outer sheath 110 is configured to house the branch portion 104 in implementations where the branch portion 104 is partially or wholly retractable into the outer sheath 110. The outer sheath 110, is also angulated with respect to the stem portion 102 in the range of 155-170 degrees. The catheter component 100 can also include an endoscopic device 112 positioned on the stem portion. The endoscopic device 112 is positioned adjacent the pre-defined bend so as to have a field of view 114 of the dissecting head 106 and the plane directly above the dissecting head 106. This assists the operator with properly placing the dissecting head 106 and the dilation balloon 108 in the submucosal tissue. The endoscopic device 112 can include a camera 113 (e.g. a digital video camera) for recording the views obtainable via the endoscopic device 112.

Figure 2:
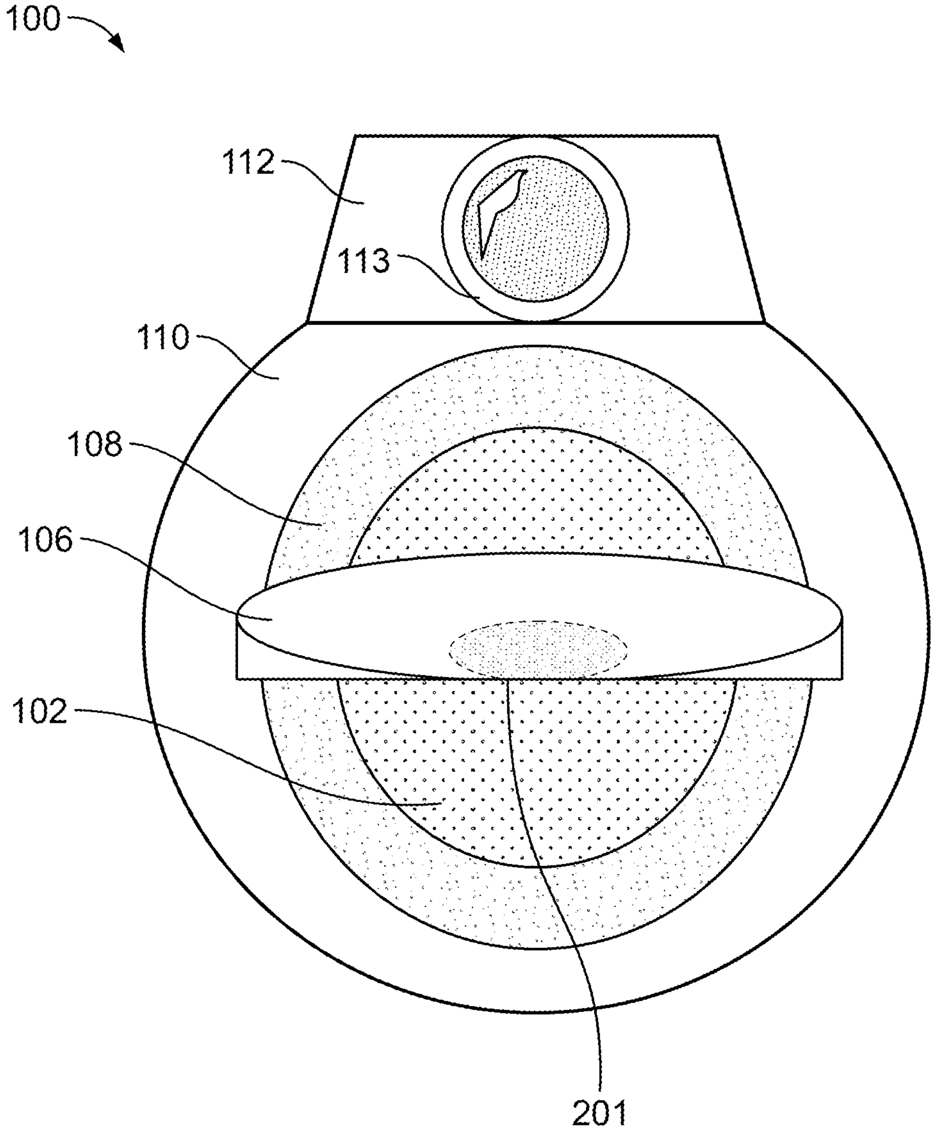
FIG. 2 illustrates a front sectional view of the drug delivery device of FIG. 1.

FIG. 2 illustrates a front sectional view of the drug delivery device of FIG. 1. The drug delivery port 201 positioned in the dissecting head 106 of the branch portion 104 is visible in FIG. 2. As shown in FIG. 2, the dissecting head 106 is sized to create an opening sufficient for the branch portion 104 to extend through, but smaller than the outer sheath 110 into which the balloon 108 can be retracted. In certain implementations, the branch portion 104 has a length in the range of 2-4 cm and a diameter in the range of. In certain implementations, the outer sheath 110 has a length in the range of 8-15 cm and a diameter in the range of 2-3 mm. The optional endoscope 112 is positioned atop the stem portion 102 to provide a view of the position of the dissecting head 106 and the dilation balloon 108. The camera 113 of the endoscope 112 allows the operator to watch the surface of the mucosa so that the operator can ensure that as the dissecting head 106 and the branch portion 104 are advanced, they are advanced backwards rather than upwards. The camera 113 allows the operator to watch the area/plane above the dissecting head 106, while the dissecting head and dilation balloon are operating in the plane below.

Figure 3A:
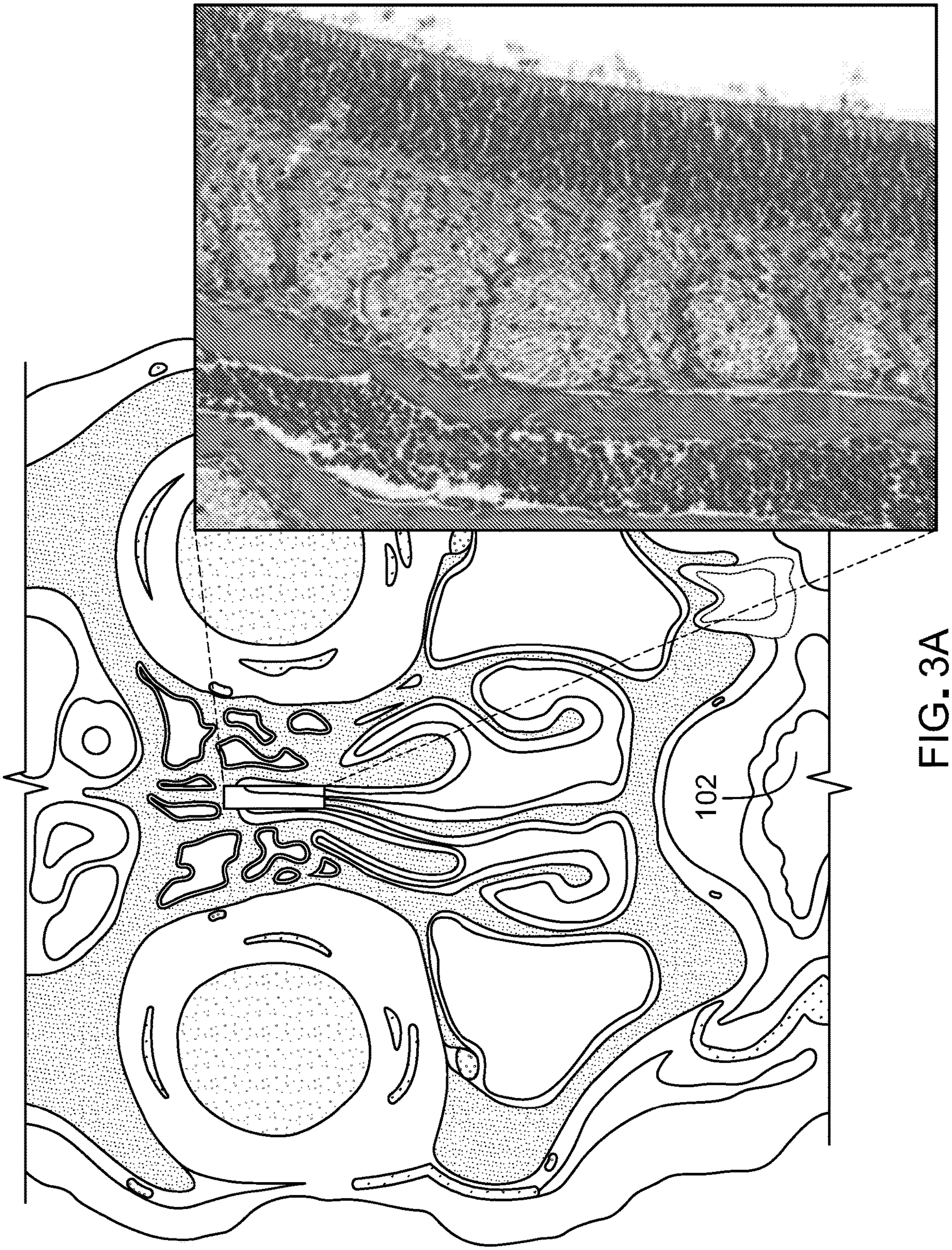
FIGS. 3A-3B show a front sectional anatomical view magnifying the submucosal, supramucoperiosteal space of the olfactory mucosa in which a drug is delivered using drug delivery devices as described herein.
Figure 3B:
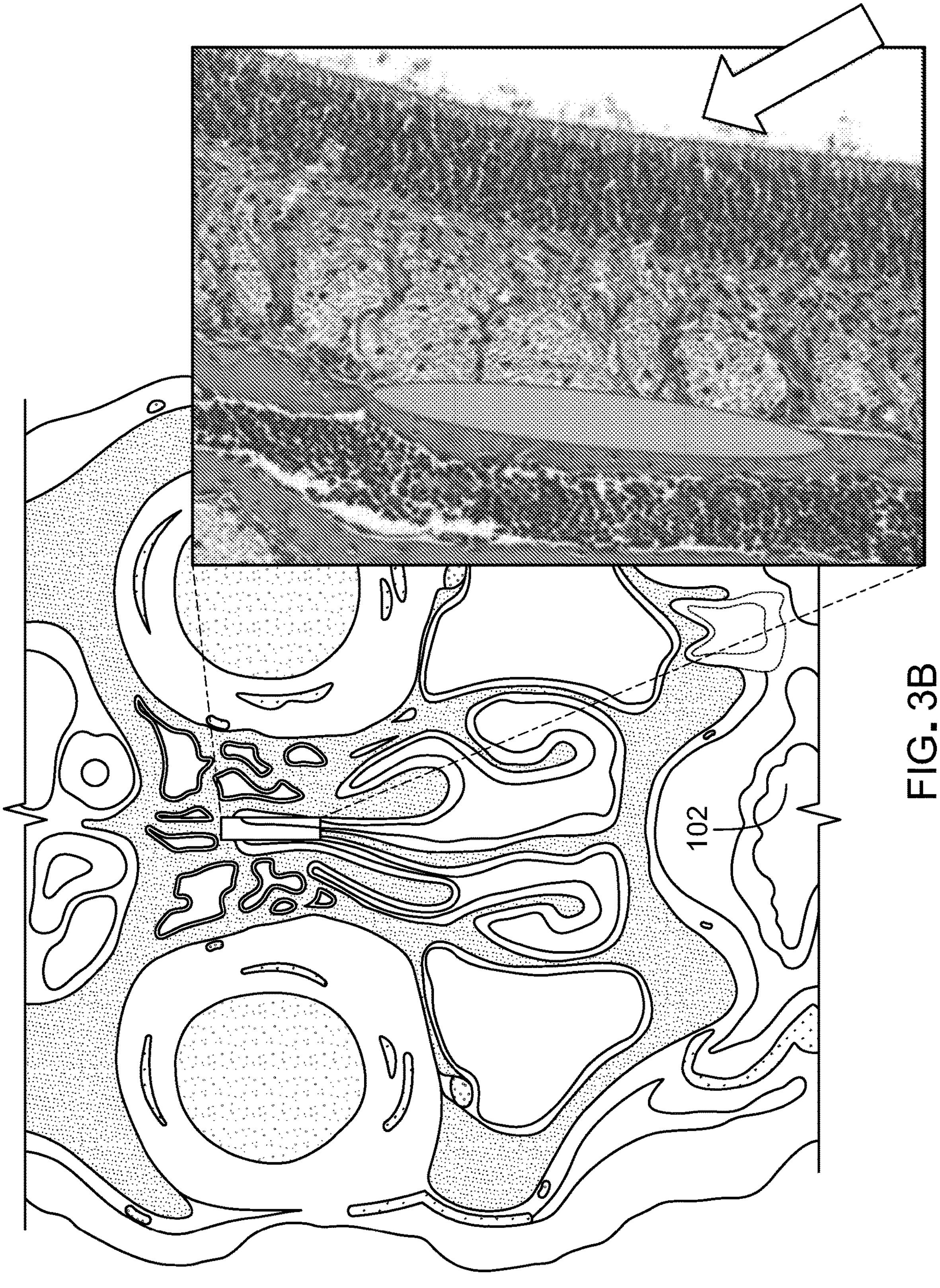

FIGS. 3A-3B show a front sectional anatomical view magnifying the submucosal, space of the olfactory mucosa in which a drug is delivered using a drug delivery device as described herein. In particular, FIG. 3A shows a magnified view of submucosal layers in which the depot for drug delivery will be created and FIG. 3B shows the depot 302 created in the mucosal layers after the depot is generated.

Figure 4A:
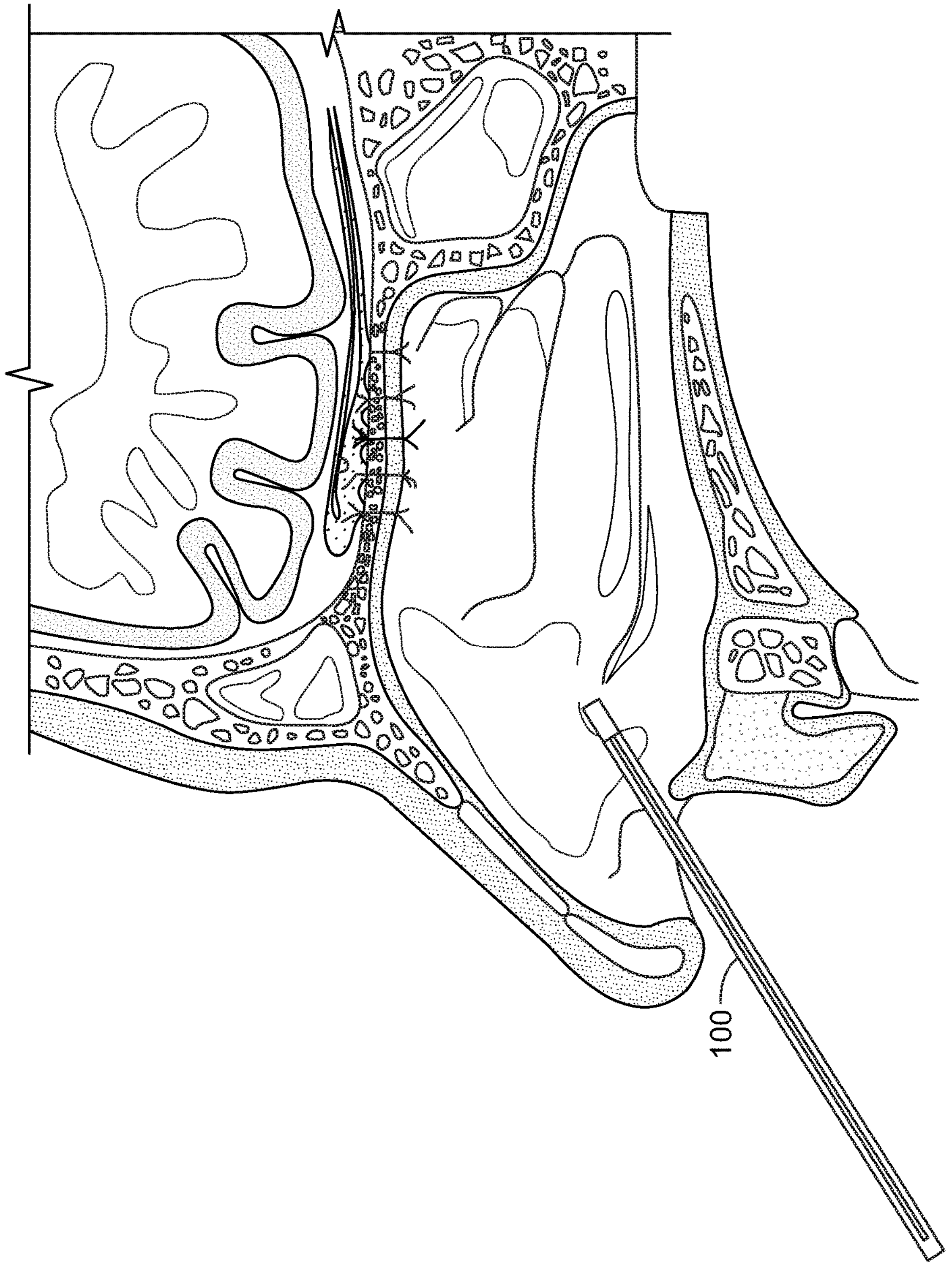
FIGS. 4A-4P illustrate a method for submucosal drug delivery via the drug delivery device of FIG. 1.
Figure 4B:
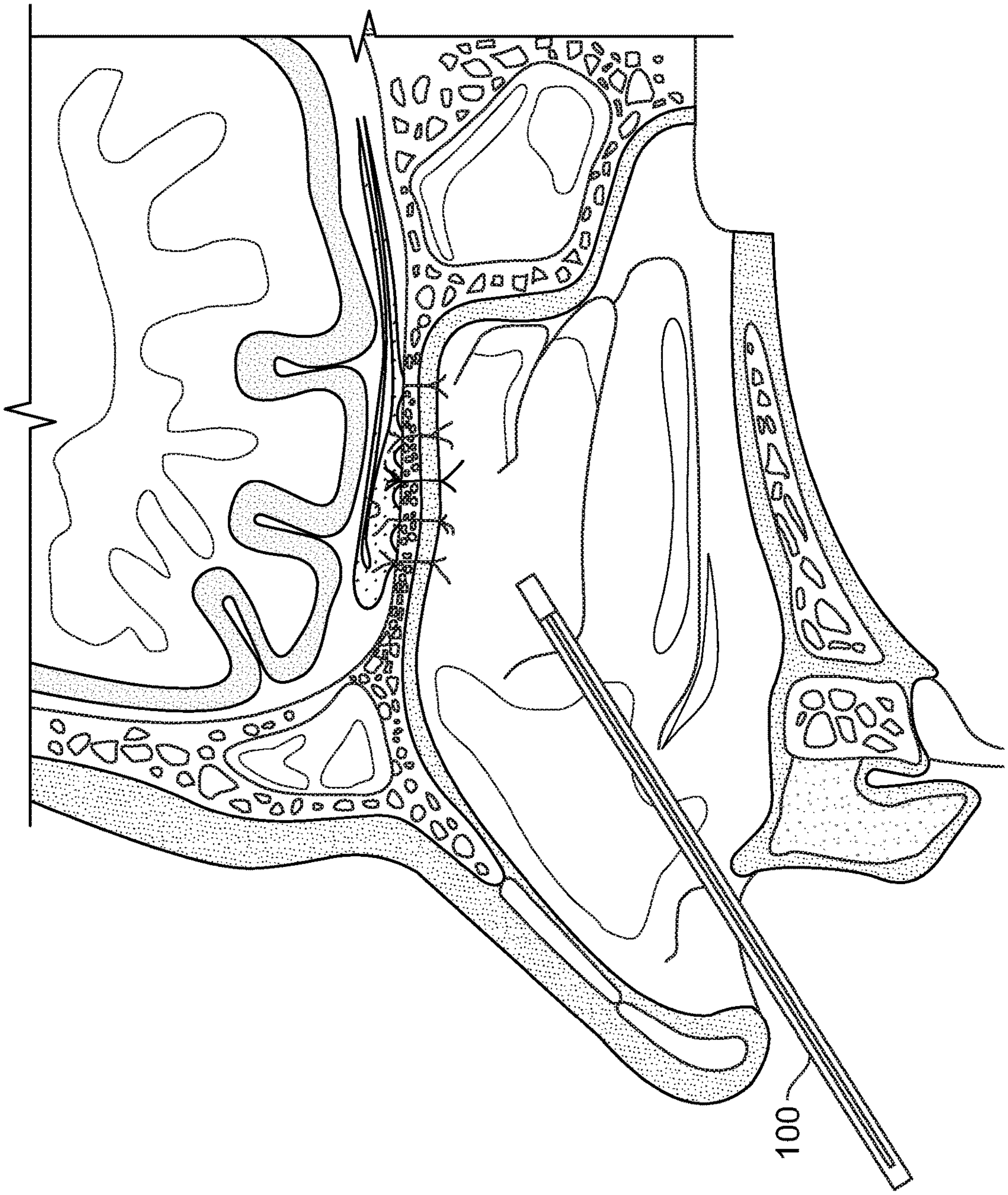
Figure 4C:
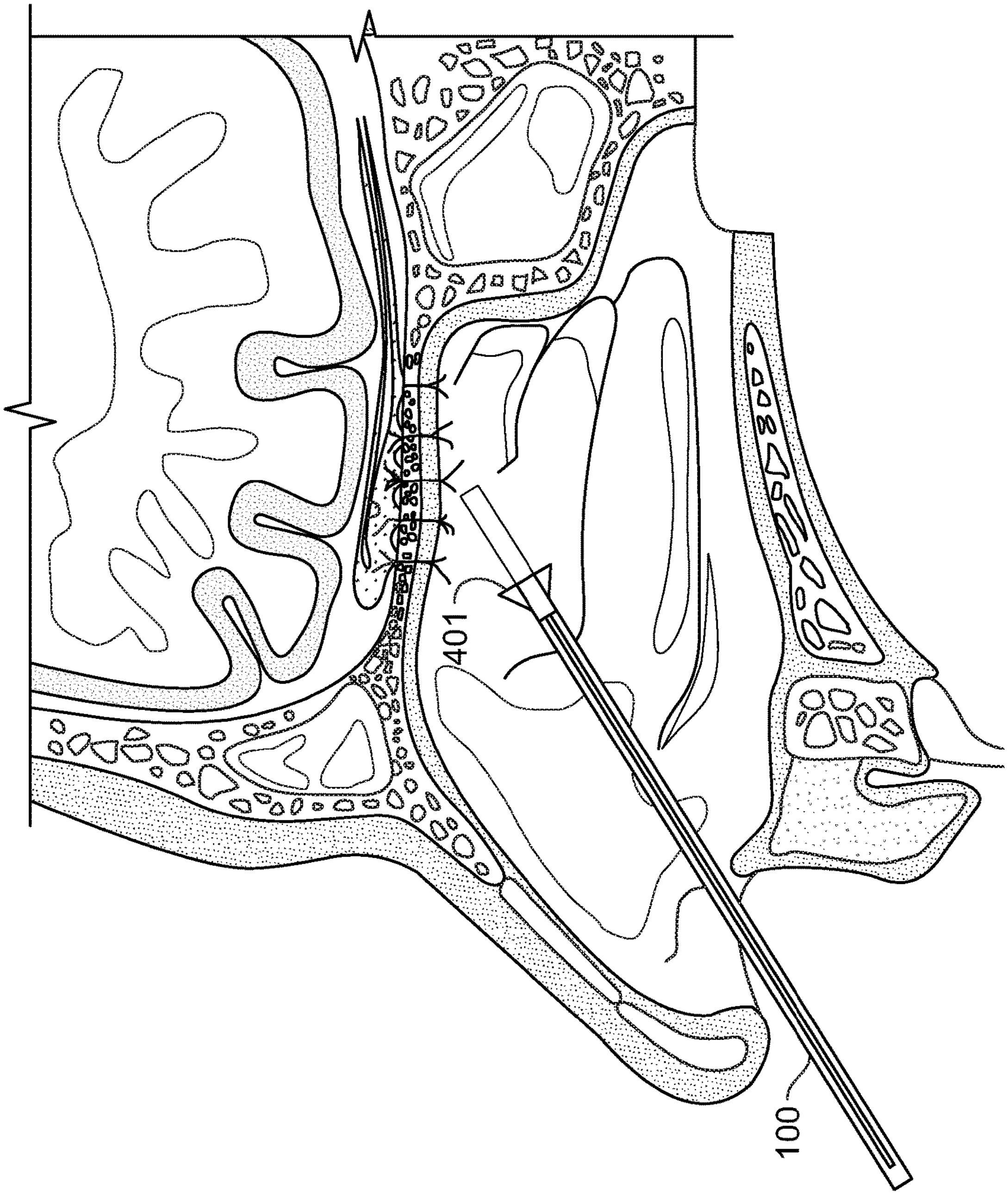
Figure 4D:
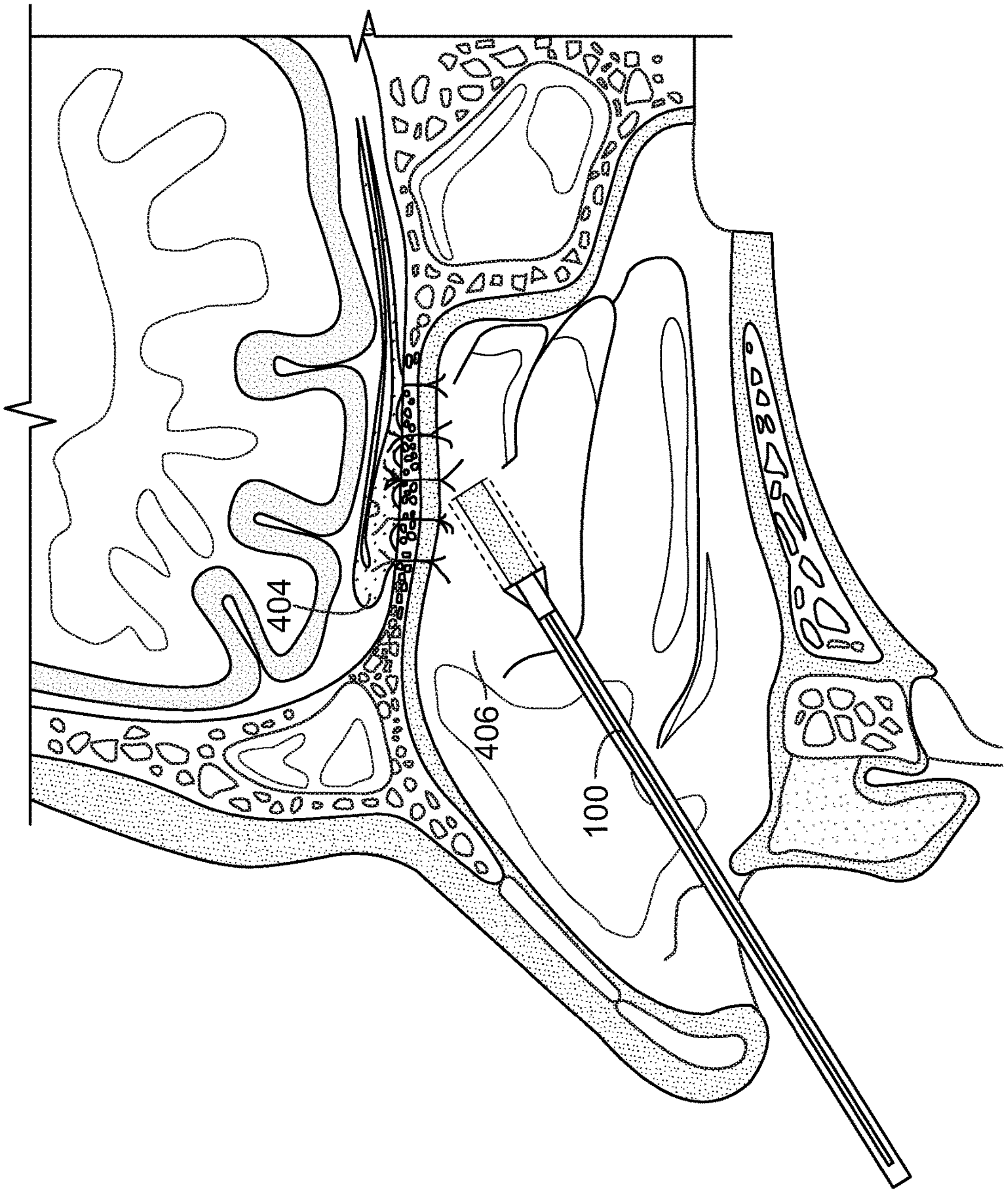
Figure 4E:
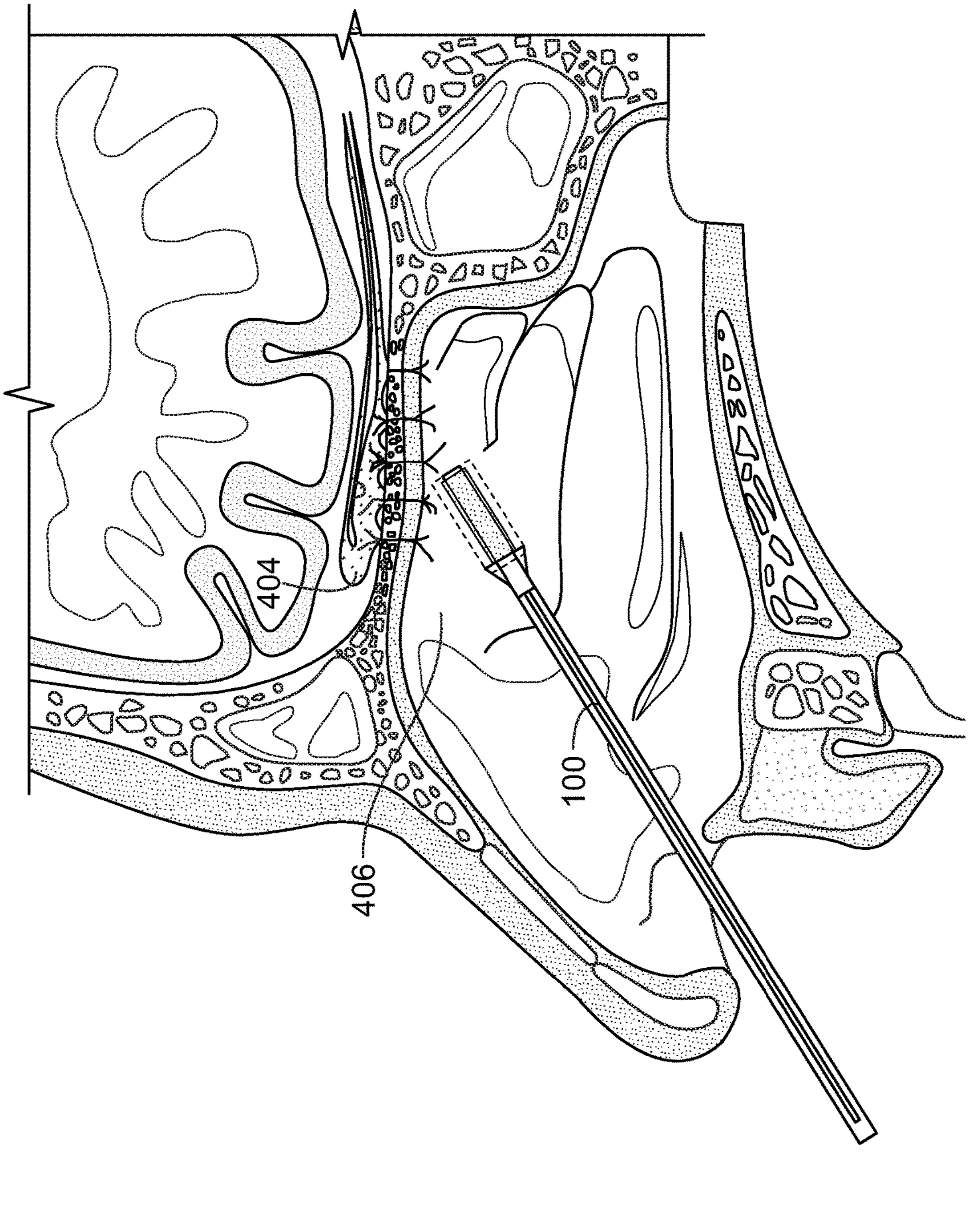
Figure 4F:
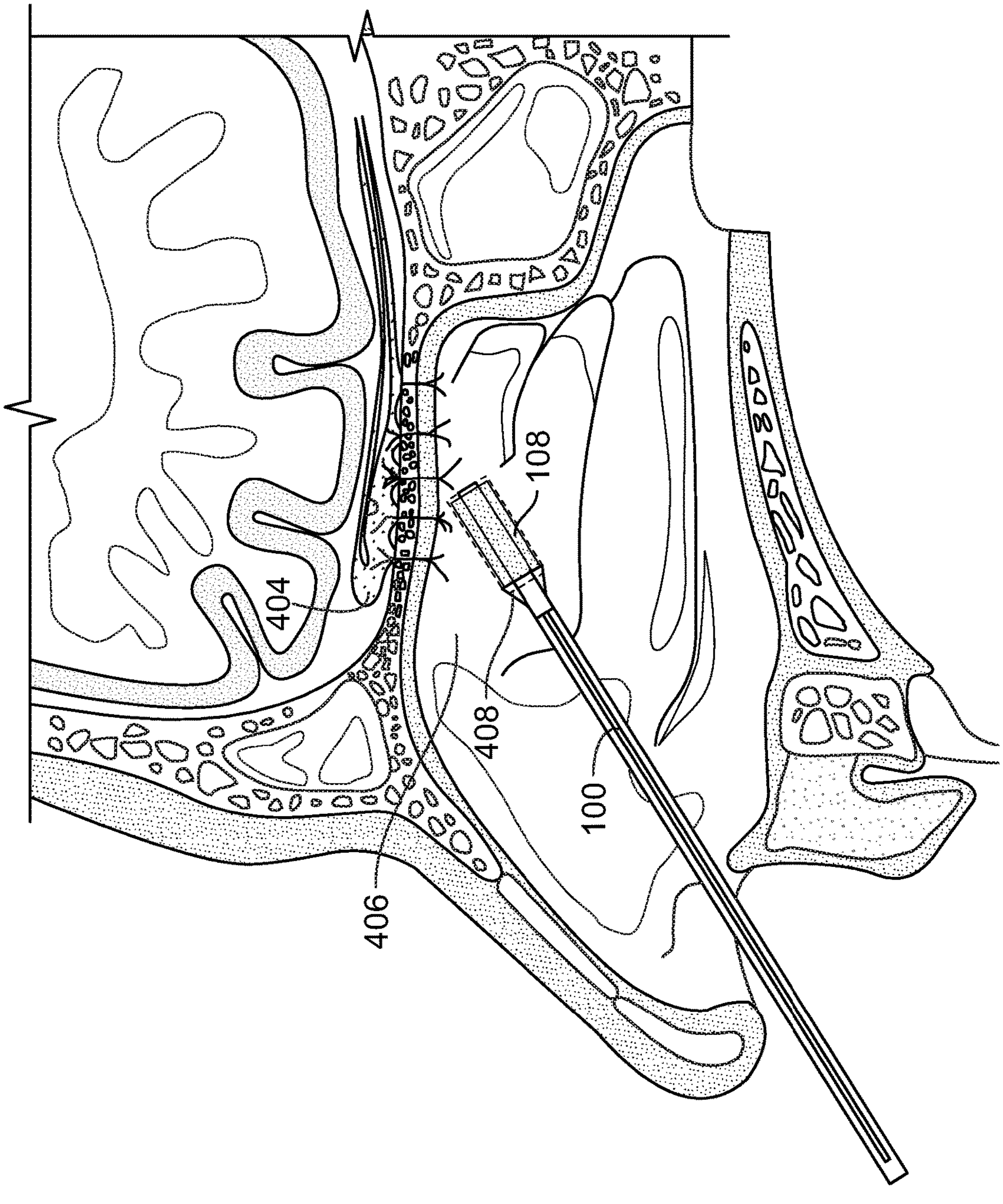
Figure 4G:
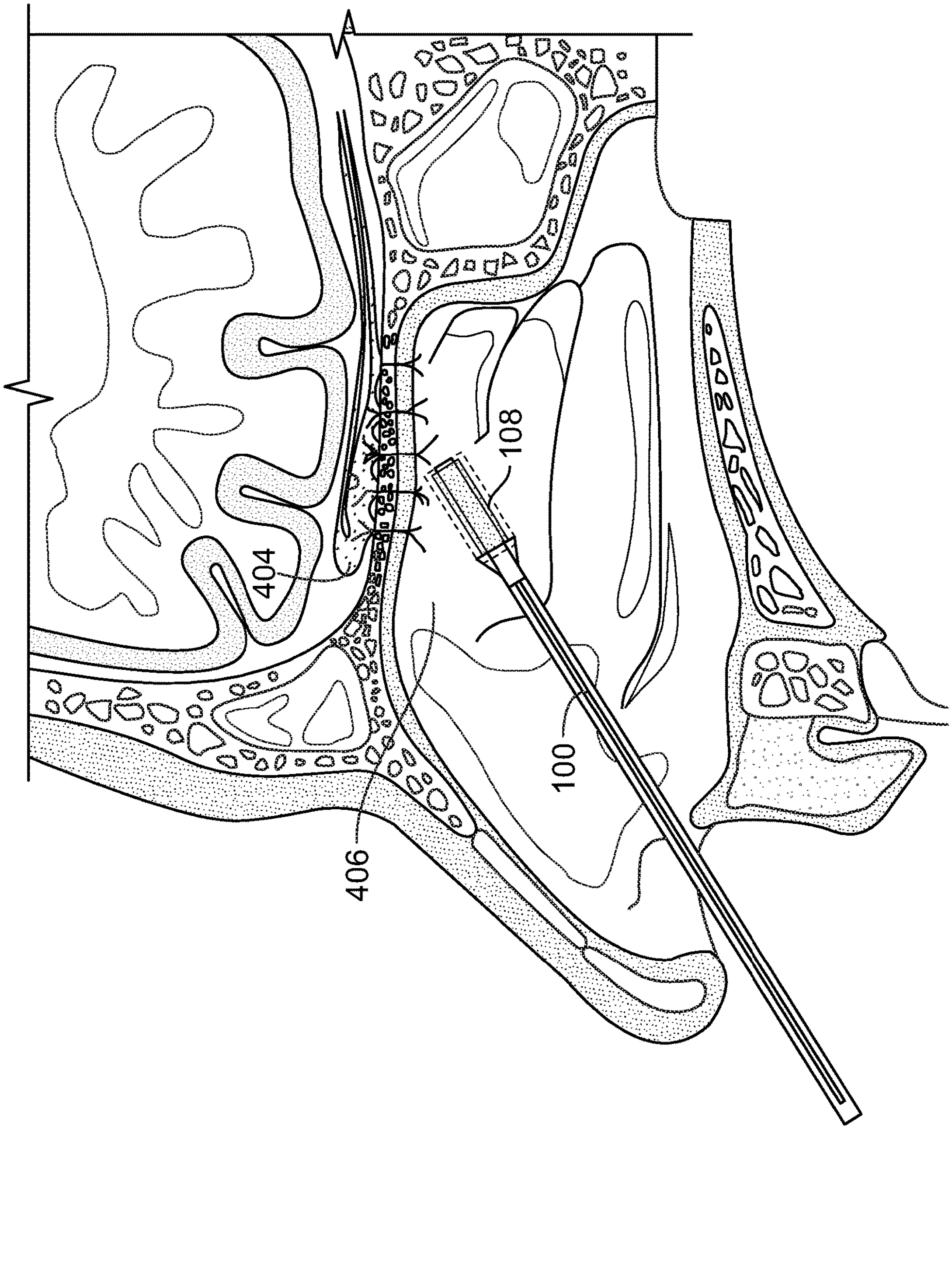
Figure 4H:
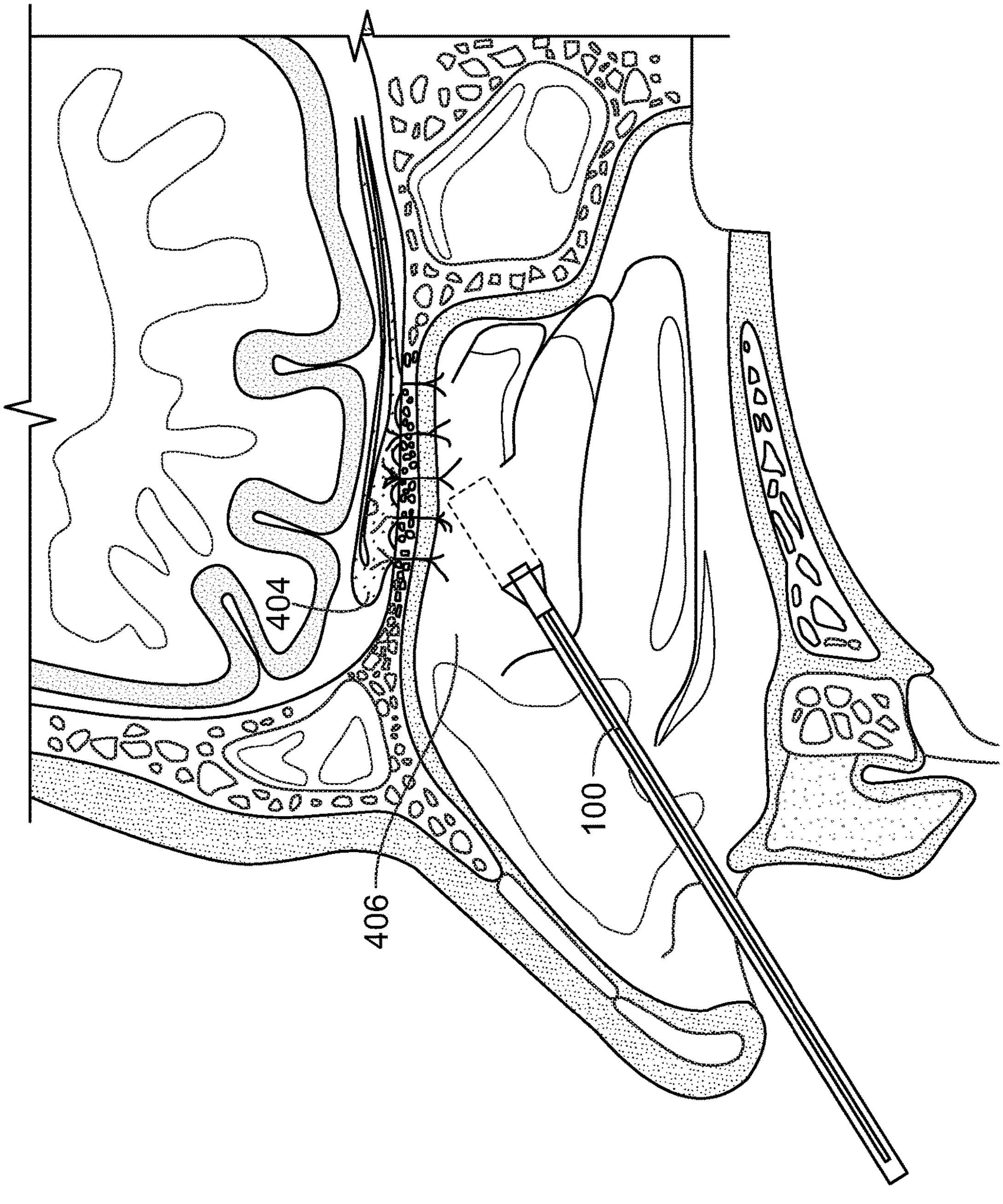
Figure 4I:
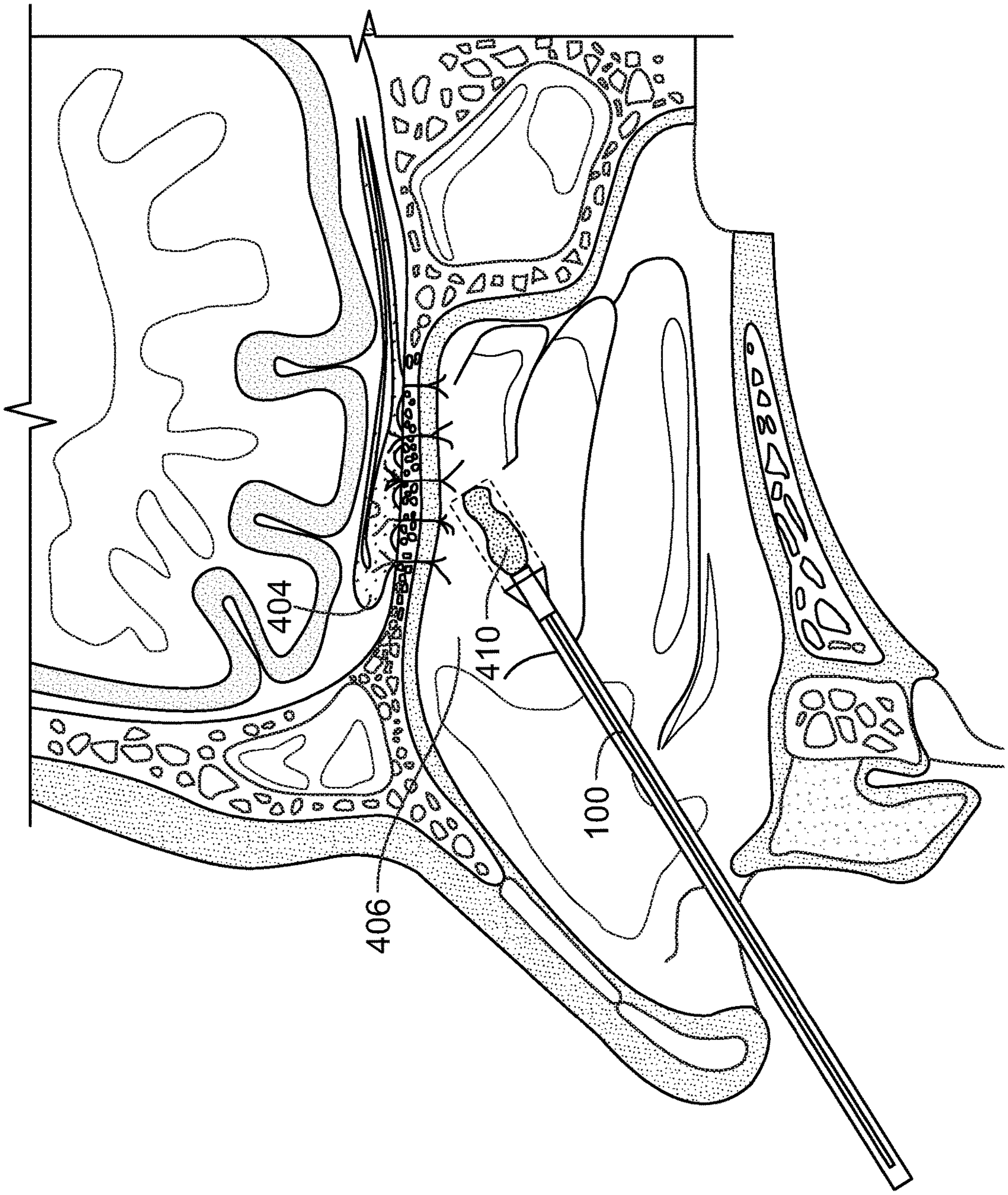

FIGS. 4A-4L illustrate a method for submucosal drug delivery via the drug delivery device of FIG. 1. In FIG. 4A, the drug delivery device 100 is inserted into the nasal cavity. In retractable configurations, the dissecting head 106 can be retracted into the outer sheath until device 100 encounters tissue to be penetrated. As shown in FIG. 4B, the drug delivery device penetrates the submucosal tissue. The dissecting head 106 is extended from the outer sheath 110 at the predefined bend angle. As demonstrated in FIG. 1, the outer sheath 110 and the branch portion are at the predefined bend angle in both the extended and the retracted position. The endoscope 110 is used for guidance during penetration, and the dissecting head 106 generates the pinhole opening through which the branch portion 104 extends. FIG. 4C shows the delivery device 100, with the branch portion 104 extending through the opening 401 created by the dissecting head 106. FIG. 4D shows the delivery device 100 with the dilation balloon 108 beginning to deploy. As shown in FIG. 4E, the branch portion 104 of the device 100 is substantially parallel to the olfactory bulb 404 and positioned in the submucosal space 406. In FIG. 4F, the dilation balloon 108 is fully deployed and thereby pushes the mucosal tissue apart to create a depot or void 408 within the tissue to be filled by the drug or therapeutic agent. In FIG. 4G, the dilation balloon 108 is contracted leaving a space in the submucosal tissue into which the therapeutic agent will be delivered. In FIG. 4H, the delivery device is retracting. During the retraction of the delivery device, for example, the branch portion 104 can be retracted at least in part into the outer sheath 110. The branch portion can be retracted such that the balloon is inside the outer sheath 110 while the dissecting head is still extending from the outer sheath and is positioned inside the depot 408 with the delivery port 201 positioned in the depot 408 or at the narrowed opening entryway into the depot 408. The outer sheath 110 may not be extended through the opening created by the dissecting head 106 in order to minimize the size of the opening and prevent the flow of the drug or therapeutic agent from the depot 408. In FIG. 4I, the drug or therapeutic agent 410 is ejected from device 100 through the delivery port 201. The therapeutic agent 410 can be pumped (e.g., via pump 115) from a reservoir 118 in or near the handle 116 through the stem portion 102 and through the branch portion 104 (e.g. via a channel or conduit extending contiguously through the stem portion 102 and 104). Accordingly, the system is operable via single-handed operation to penetrate, space, and inject. The therapeutic agent 410 can also be contained in vial or cartridge that can be coupled to device 100 and pumped from the cartridge through the stem and branch portions 102, 104 respectively and out of the delivery port 201. In certain implementations, the device 100 includes two plungers **117*a* and 117*b* in the handle a first plunger 117a for inflating and deflating the dilation balloon and a second plunger 117*b* for injecting the therapeutic agent 410. For example, the device 100** can be configured as a syringe.

Figure 4J:
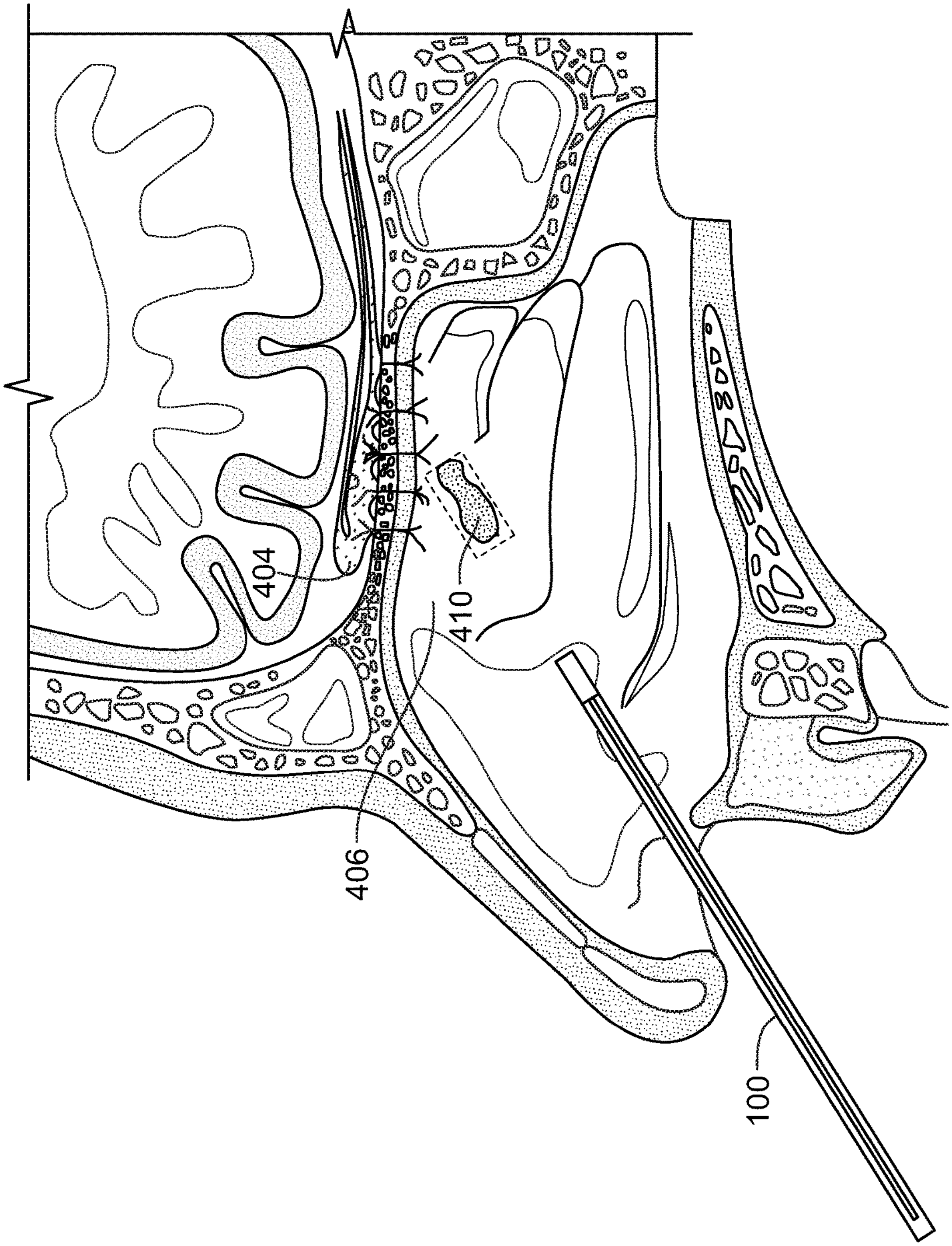
Figure 4K:
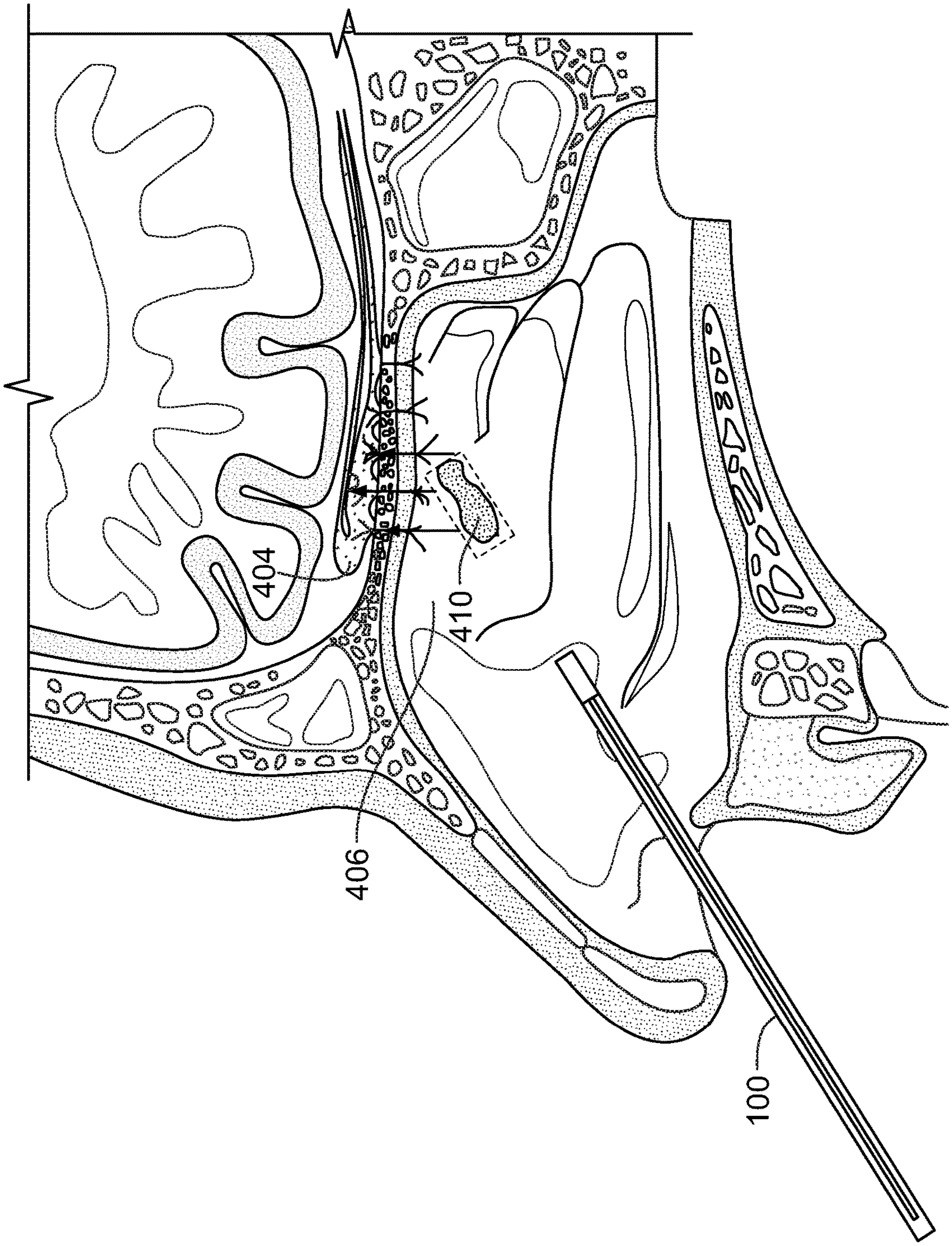
Figure 4L:
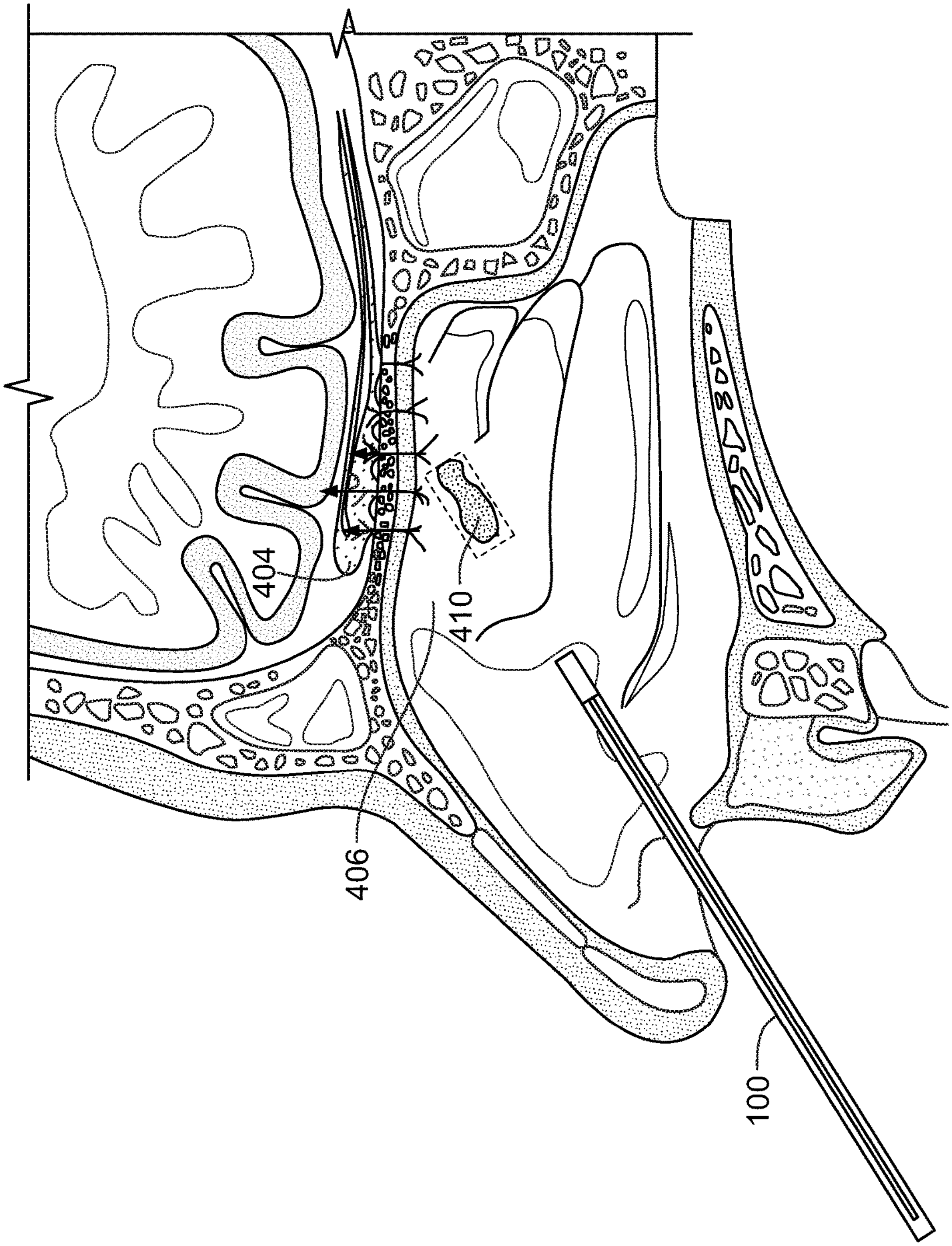

In FIG. 4J the device 100 is substantially removed from the depot 408, and in FIG. 4K the therapeutic agent 410 is diffused into the central nervous system via the olfactory bulb 404. In FIG. 4L, the agent 410 retained in the depot 408 is reduced further as uptake into the central nervous system increases over time. Accordingly, embodiments of the present invention provide an alternative method of treating conditions affecting the central nervous system that presently warrant general anesthesia, surgery, and/or intrathecal injections. The devices and methods afforded by implementations disclosed herein limit drug leak out, thereby increasing the efficacy and allowing a precise amount of a drug or therapeutic agent to be administered.

Figure 4M:
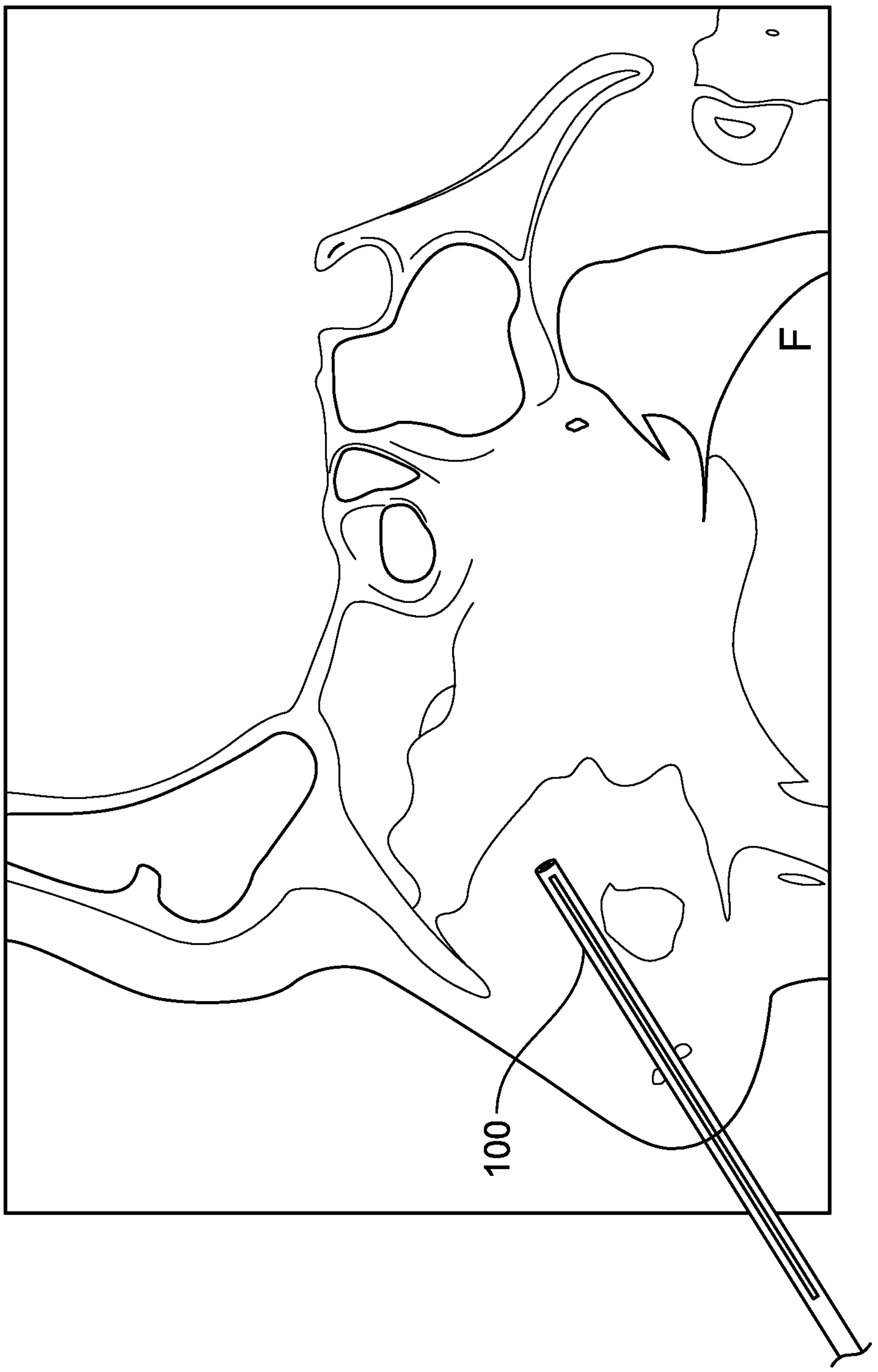
Figure 4N:
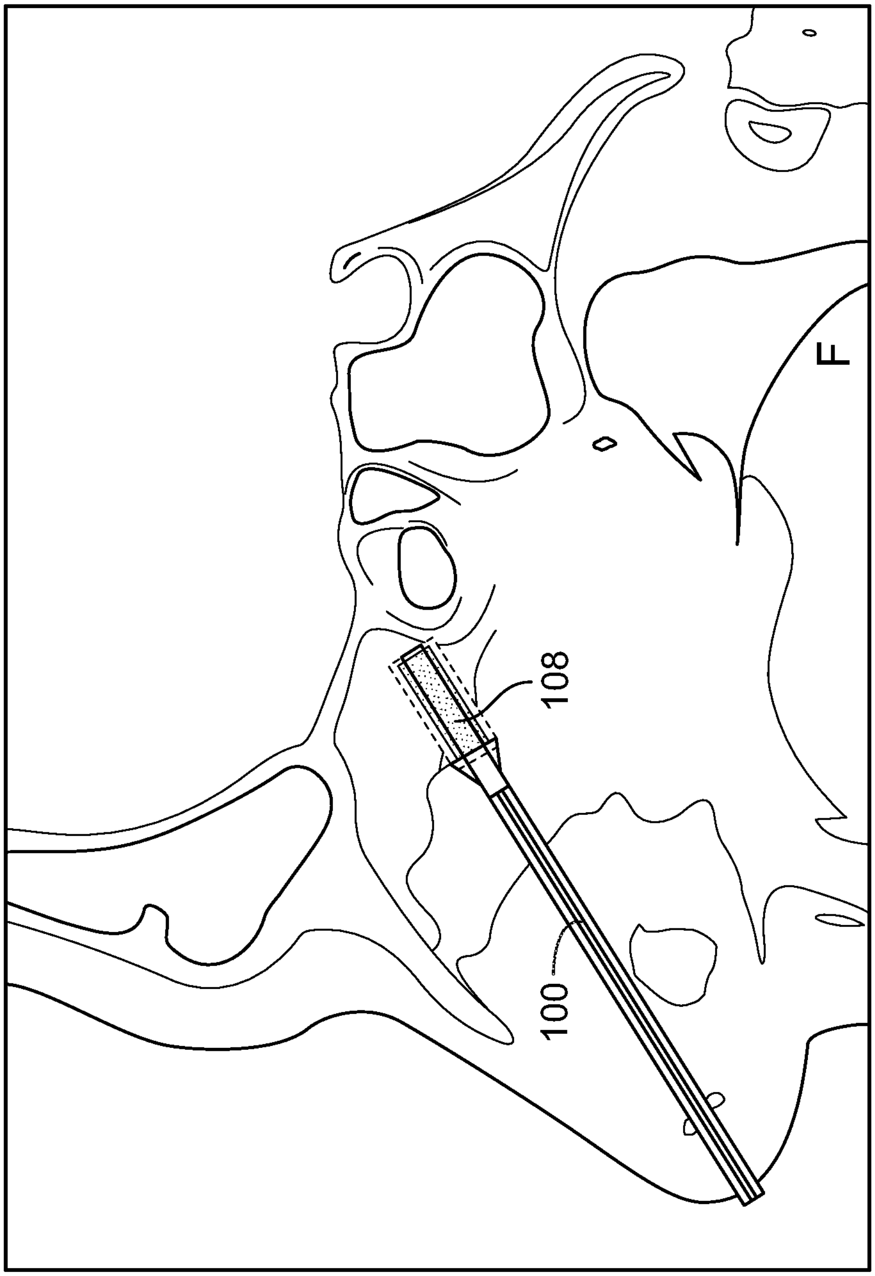
Figure 4O:
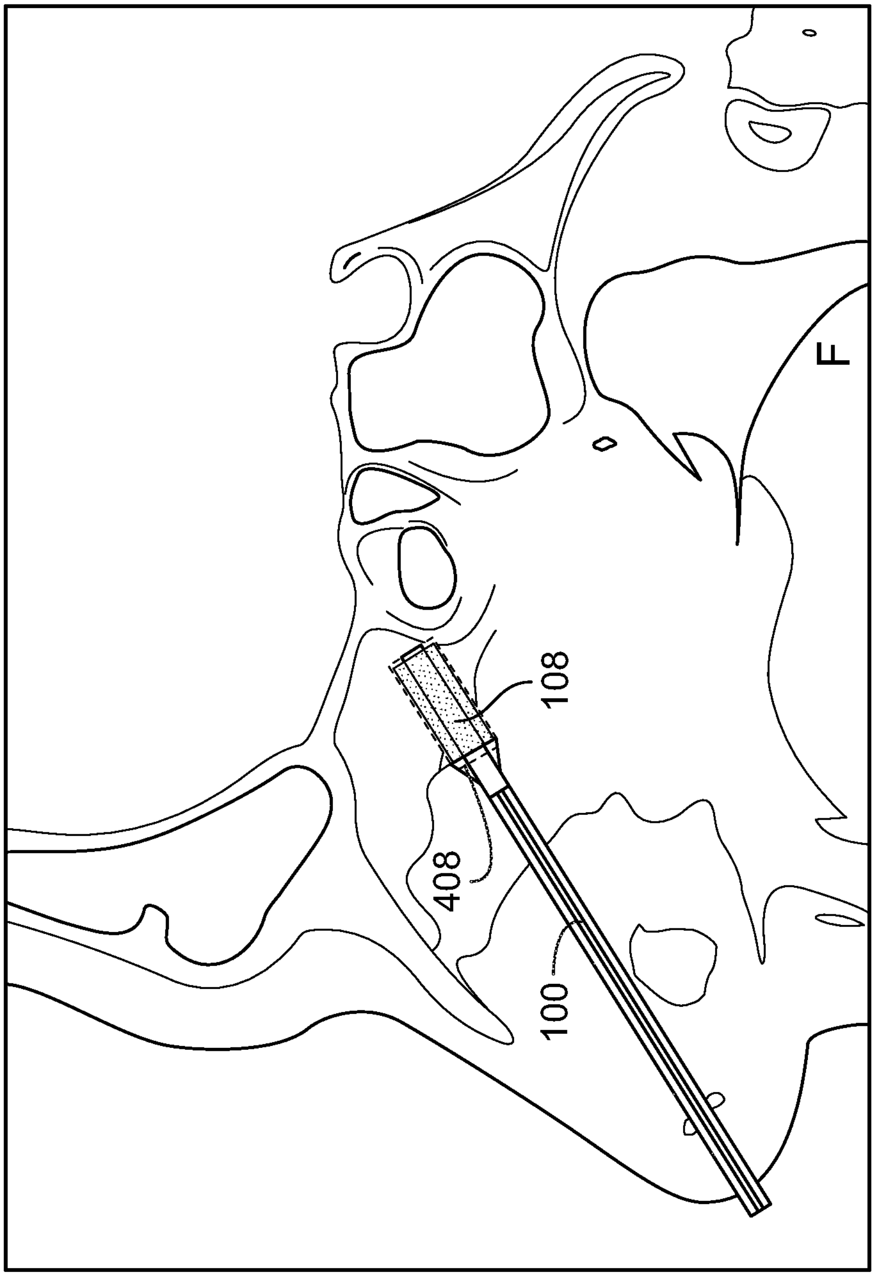
Figure 4P:
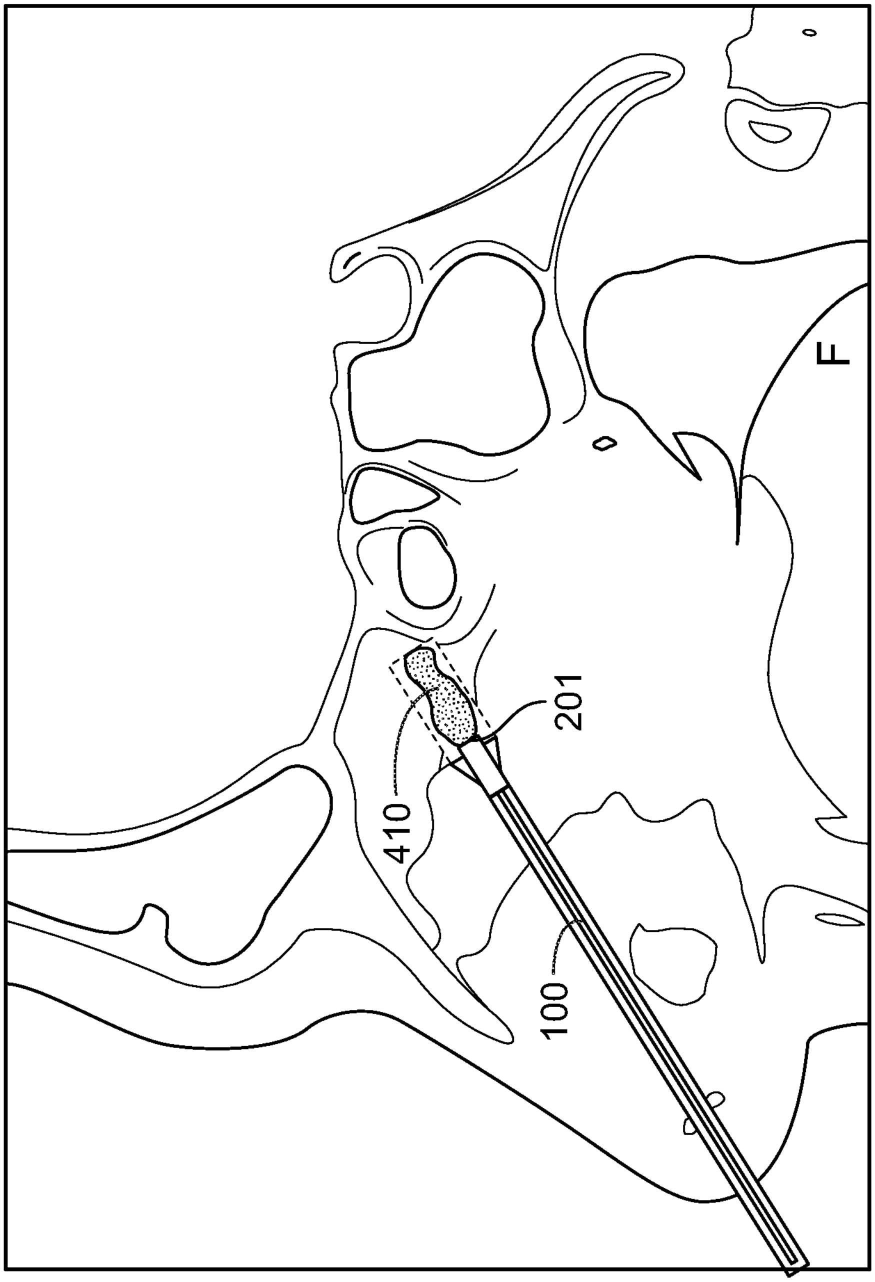

FIGS. 4M-4P illustrate the method for submucosal drug delivery of FIGS. 4A-4L depicted by a CT scan along the septum. In FIG. 4M, the drug delivery device 100 is inserted into the nasal cavity. In FIG. 4N, the dilation balloon 108 of the delivery device 100 is beginning to deploy. In FIG. 4O, the dilation balloon 108 is fully deployed and thereby pushes the mucosal tissue apart to create a depot or void 408 within the tissue to be filled by the drug or therapeutic agent. In FIG. 4P, the delivery device 100 is partially retracted (e.g. into the outer sheath) and the drug or therapeutic agent 410 is ejected from device 100 through the delivery port 201.

Figure 5A:
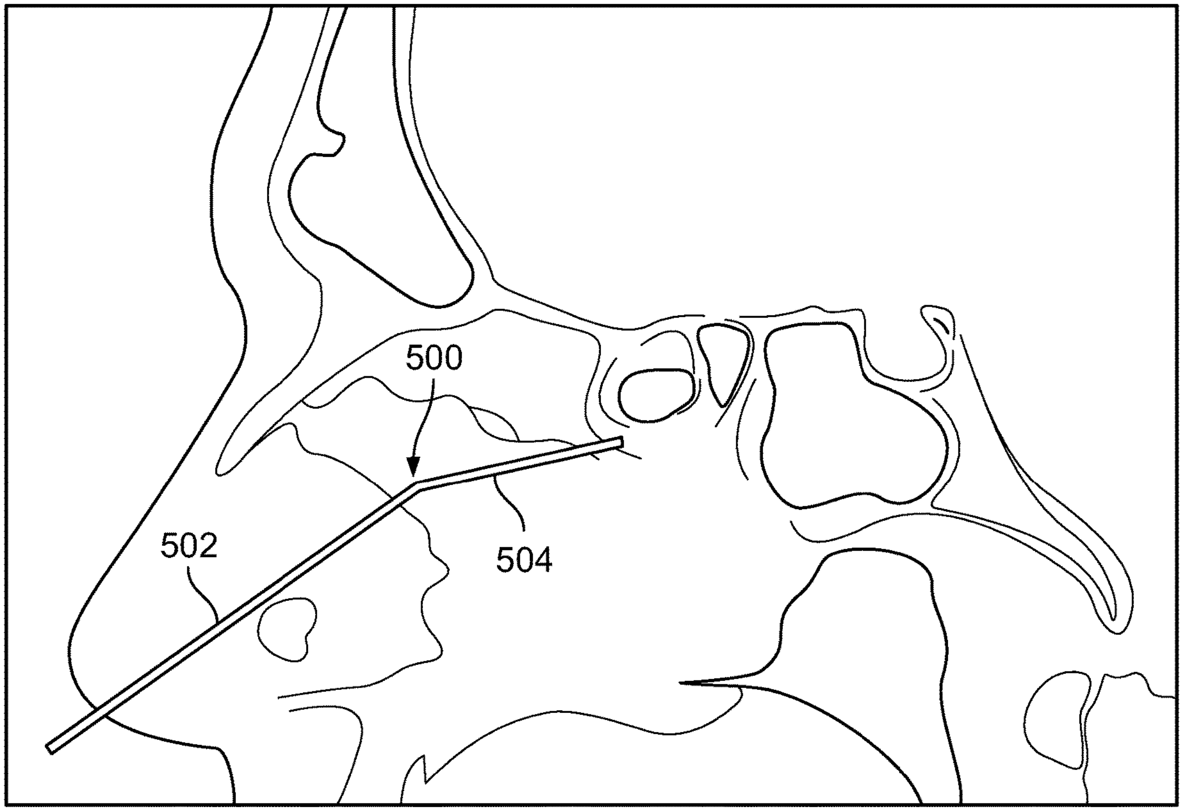
FIGS. 5A-5B illustrate a drug delivery device according to particular implementations.
Figure 5B:
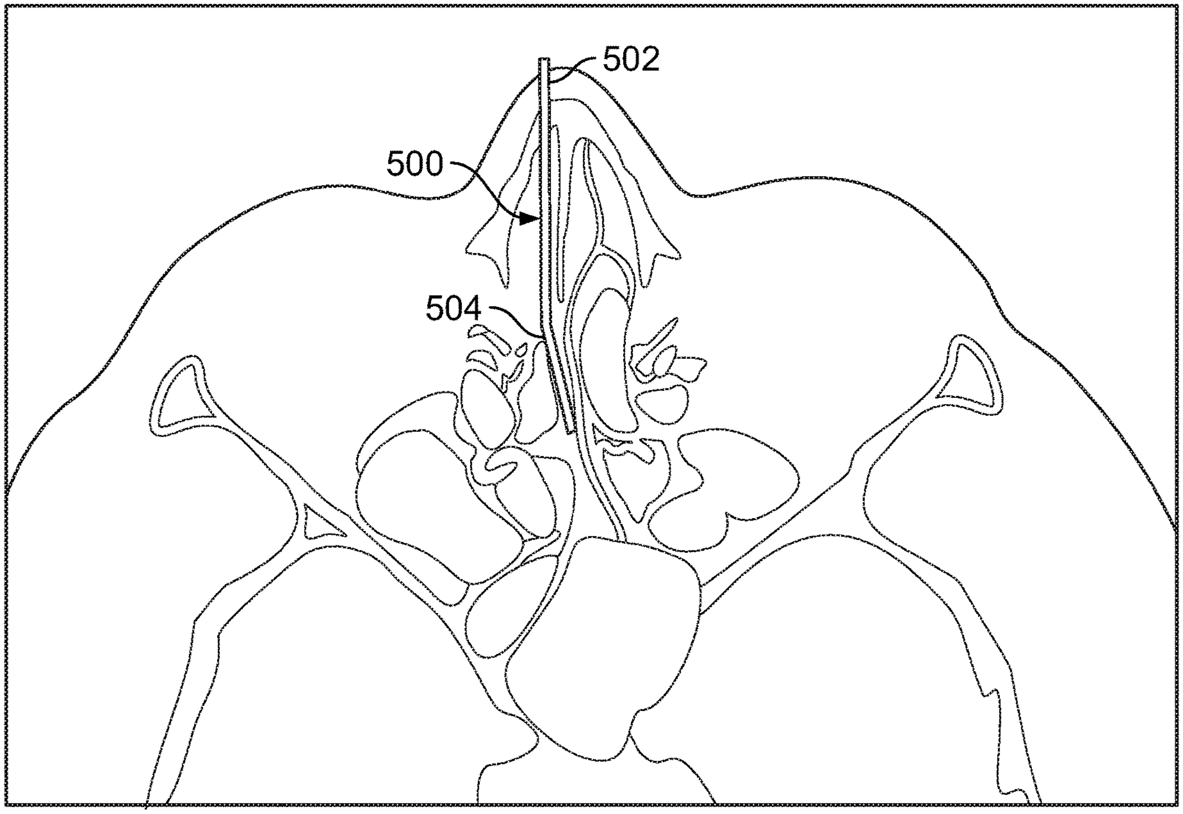

FIGS. 5A-5B illustrate a drug delivery device according to particular implementations. In FIG. 5A, the drug delivery device 500 is positioned in the submucosal space for depot delivery of a therapeutic agent in a manner similar to device 100. As shown in FIG. 5A, the branch portion 504 of the device 500 is substantially parallel to the olfactory bulb and positioned in the submucosal space. As demonstrated in FIG. 5B, which provides a top view of the drug delivery device 500 in the submucosal space, in certain implementations the drug delivery device 500 can be angled about a second axis. Accordingly, the device is also configured for extending inwardly through the nasal cavity to reach the submucosal space.

Figure 6:
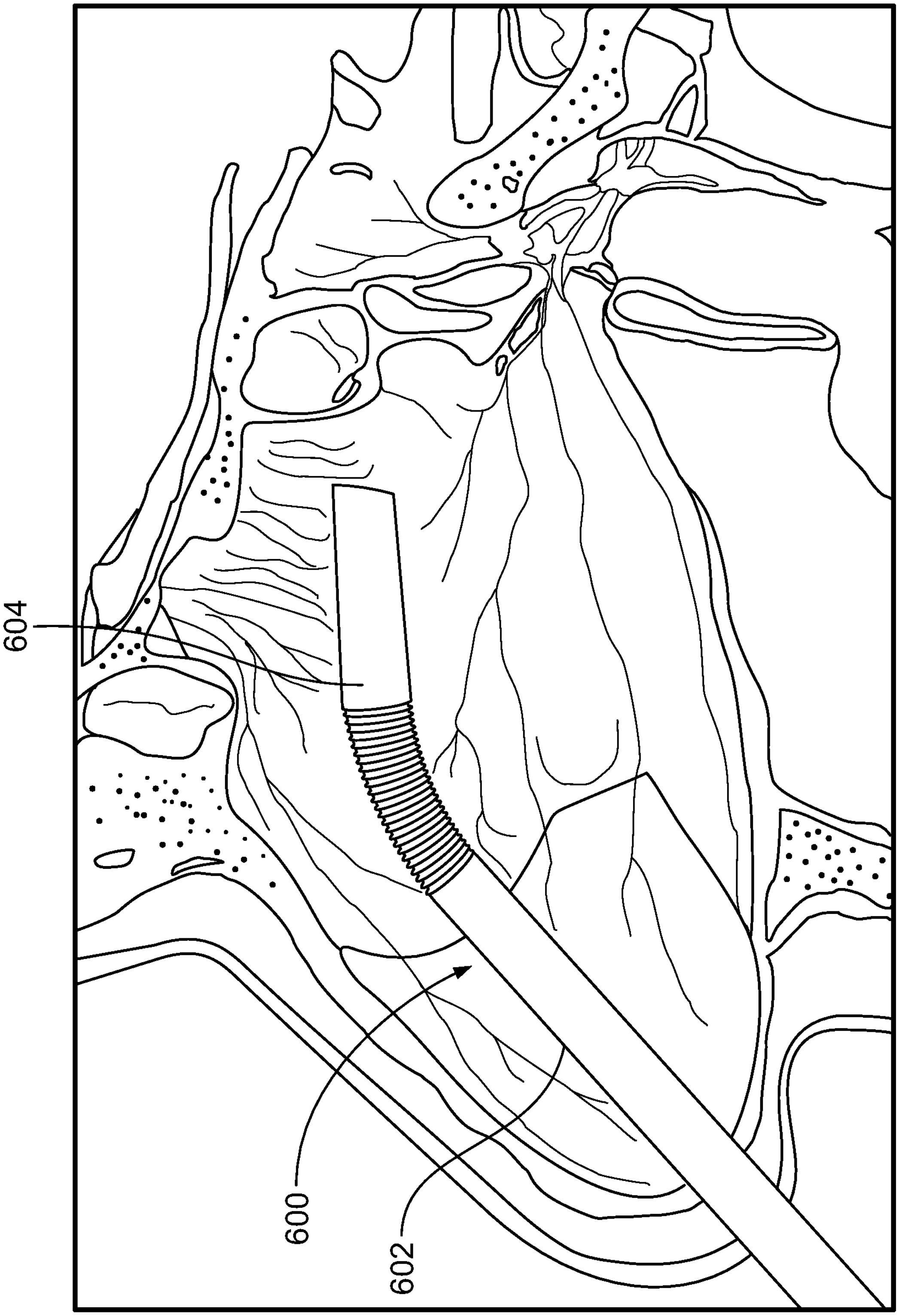
FIG. 6 shows a side sectional view of another drug delivery device according to certain implementations.

FIG. 6 shows a side sectional view of another drug delivery device according to certain implementations. As illustrated in FIG. 6, a drug delivery device 600 can be configured to flex and thereby change the degree of the obtuse angle between a branch portion 604 and a stem portion 602 of the cannulated drug delivery device 600. The flexibility can be provided about more than one axis in particular implementations.

Figure 7:
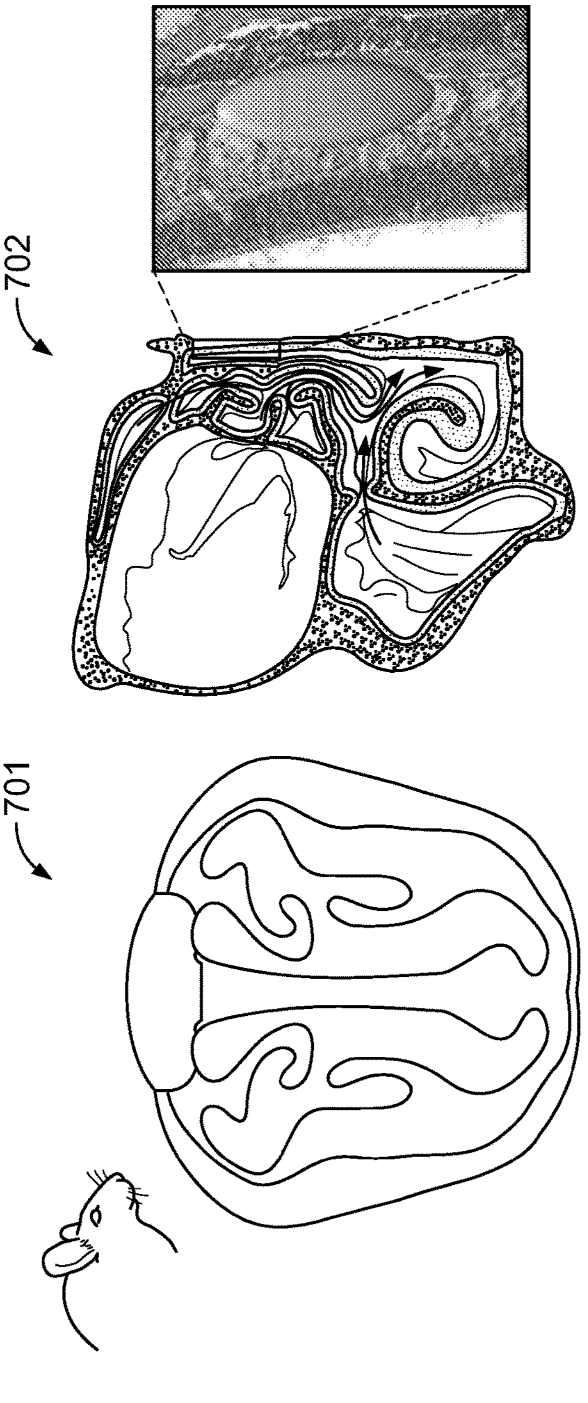
FIG. 7 illustrates a cross sectional illustration of a rat model of a depot.
Figure 9:
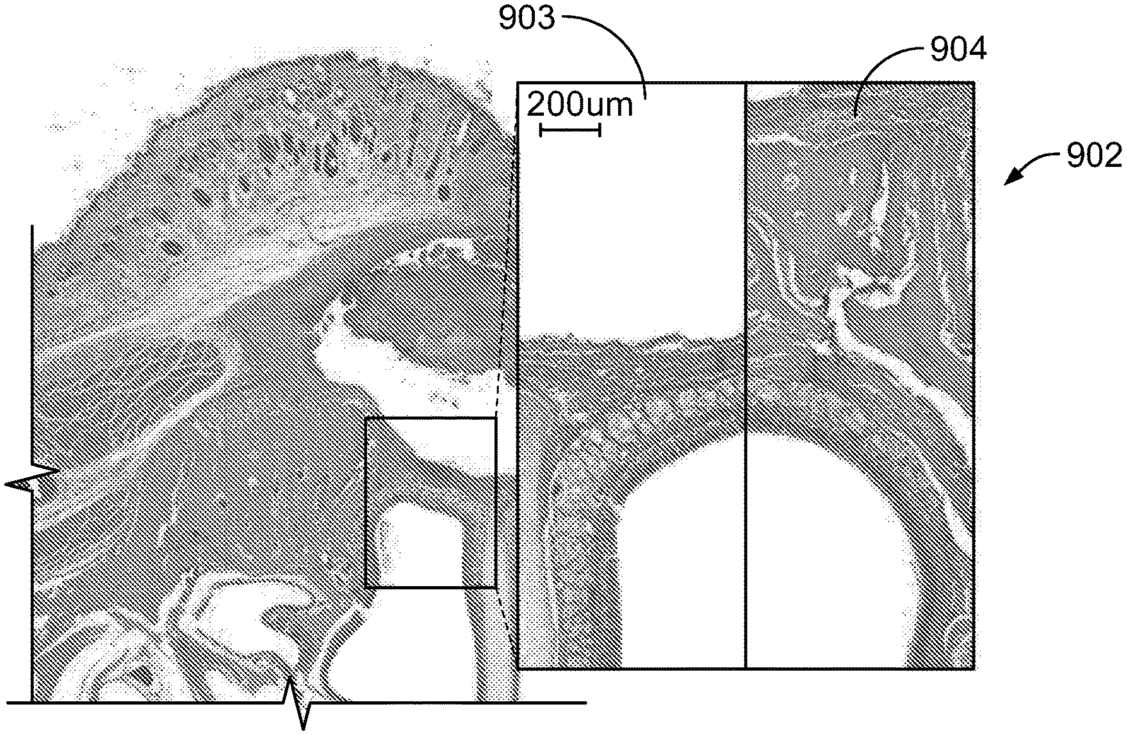
FIG. 9 is a cross sectional histological view (H&E) of the rat model depicted in FIG. 7 at low and high magnification.

FIG. 7 illustrates a cross sectional illustration of rat model of a depot. In the rat model 701, the depot is delivered where the dorsal nasal bone is removed (as shown in FIG. 9) from the rat to expose the mucoperichondrium of the nasal and olfactory rodent mucosa. The depot is then applied to this surface, which is anatomically identical to the submucosal space in the human model 702.

Figure 8:
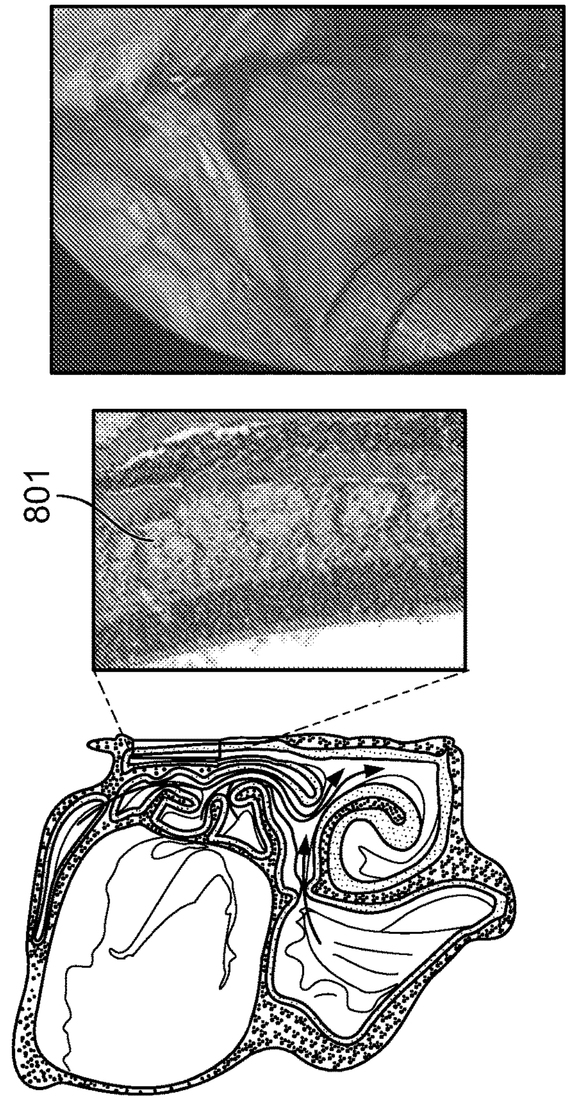
FIG. 8 shows an endoscopic view of the olfactory submucosal space with an olfactory nerve trunk (labeled) seen extending from the intracranial space into the submucosal space.

FIG. 8 shows an endoscopic view of the olfactory submucosal space with an olfactory nerve trunk 801 seen extending from the intracranial space into the submucosal space. This space represents the potential space where the depot will be dosed.

FIG. 9 is a cross sectional histological view (H&E) of the rat model 701 depicted in FIG. 7 at low and high magnification. The split expanded box 902 represents the post surgical view 903 and pre-surgical view 904 (bar=250 microns) before and after dorsal nasal bone removal.

Figure 10:
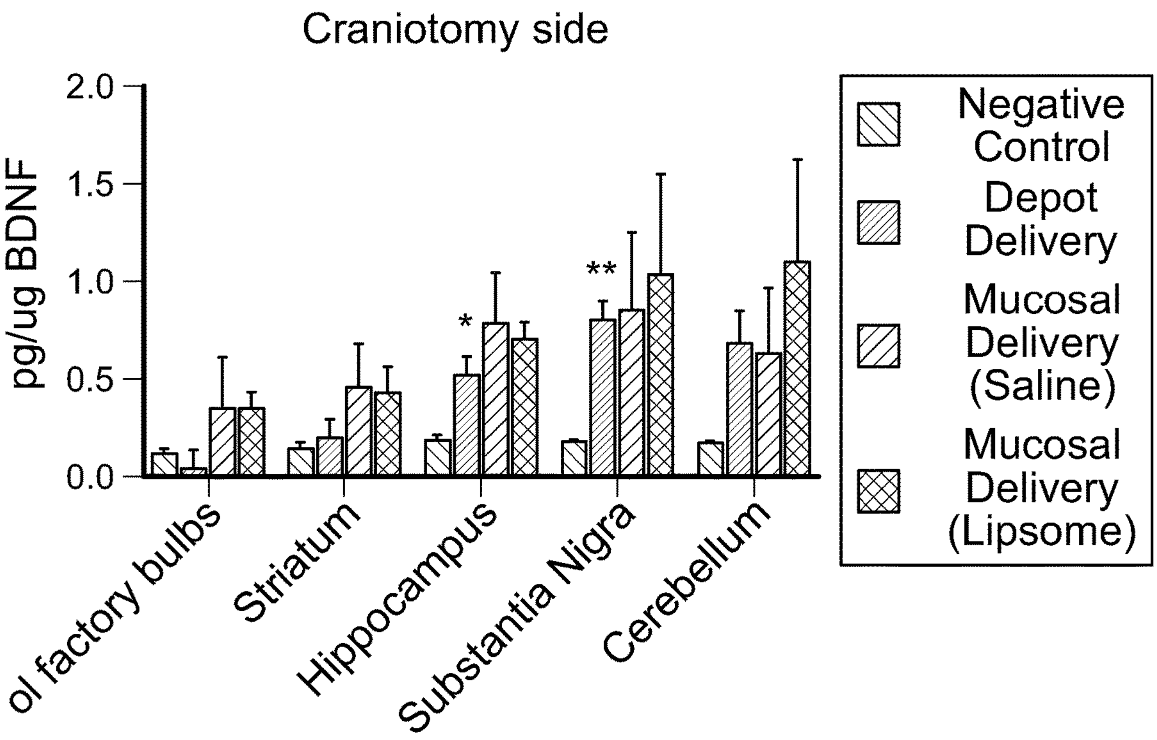
FIG. 10 shows a comparison of ipsi-lateral brain-derive neurotrophic factor, BDNF, upregulation (e.g. craniotomy side) following BDNF AntagoNAT (0.15 mg/kg) delivery.

FIG. 10 shows a comparison of ipsi-lateral BDNF upregulation (e.g. craniotomy side) following BDNF AntagoNAT (0.15 mg/kg) delivery via a mucosal graft in saline or liposome, versus minimally invasive nasal depot (MIND), versus saline control in various brain subregions. The depot approach results in significant BDNF upregulation relative to control in hippocampus and substantia nigra relative to negative control.

Figure 11:
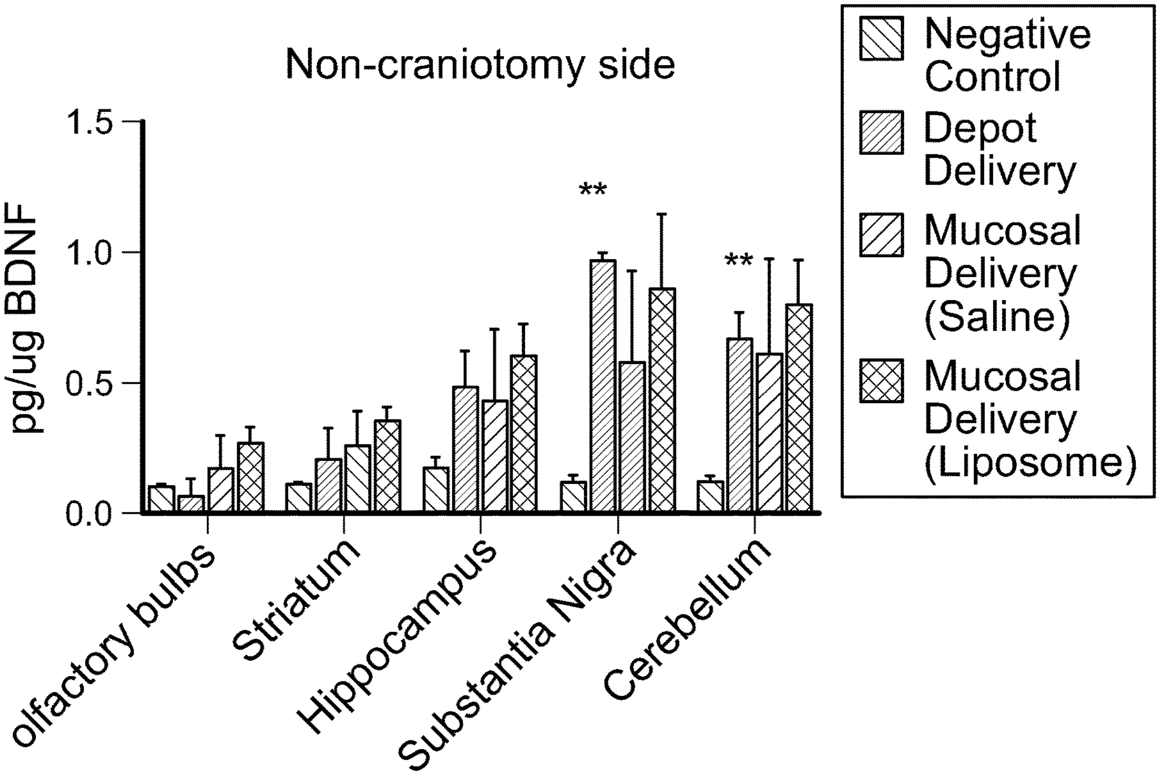
FIG. 11 shows a comparison of contra-lateral BDNF upregulation (e.g. non-craniotomy side) following BDNF AntagoNAT (0.15 mg/kg) delivery.

FIG. 11 shows a comparison of contra-lateral BDNF upregulation (e.g. non-craniotomy side) following BDNF AntagoNAT (0.15 mg/kg) delivery via a mucosal graft in saline or liposome, versus minimally invasive nasal depot (MIND), versus saline control in various brain subregions. The depot approach results in significant BDNF upregulation relative to control in substantia nigra and cerebellum relative to negative control.

Figure 12:
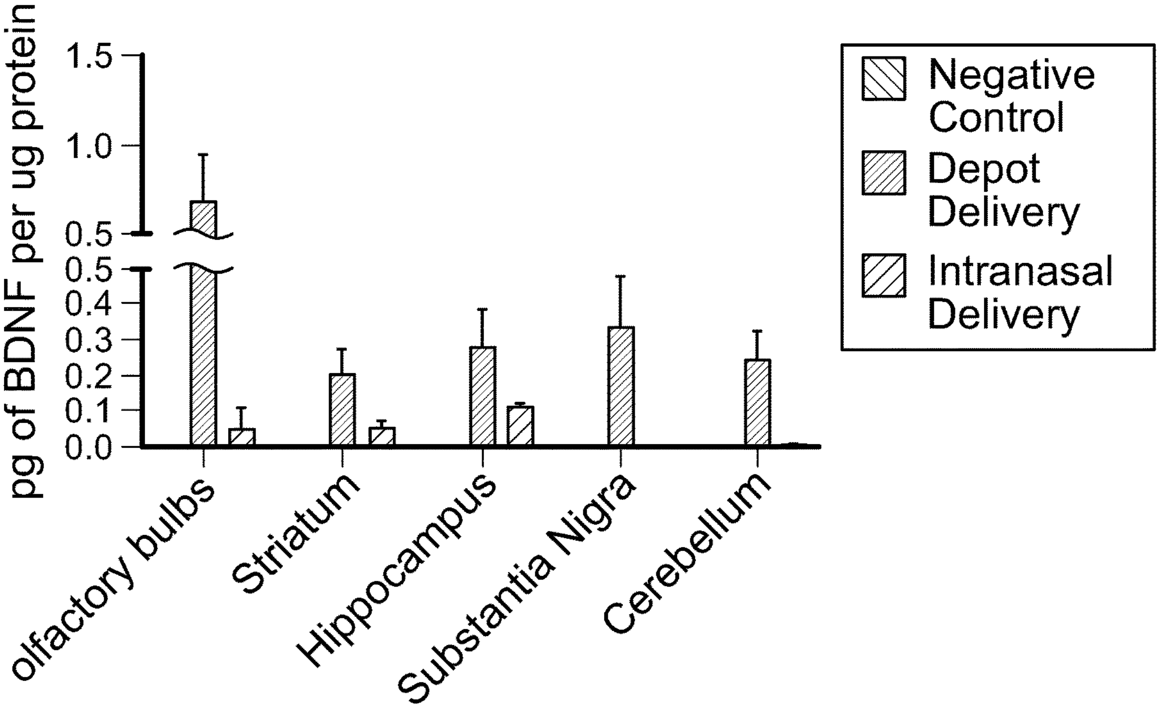
FIG. 12 shows a comparison of, BDNF, AntagoNAT (0.15 mg/kg, 60 micL) distribution in the rat brain following depot delivery versus traditional nasal irrigation and negative saline control.

FIG. 12 shows a comparison of BDNF AntagoNAT (0.15 mg/kg, 60 micL) distribution in the rat brain following depot delivery versus traditional nasal irrigation and negative saline control demonstrating increased distribution in all regions examined using the minimally invasive nasal depot (MIND) technique.

Other Embodiments

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub combination. Moreover, although features may be described above as acting in certain combinations and even initially claimed as such, one or more features from a claimed combination can in some cases be excised from the combination, and the claimed combination may be directed to a sub combination or variation of a sub combination.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub combination. Moreover, although features may be described above as acting in certain combinations and even initially claimed as such, one or more features from a claimed combination can in some cases be excised from the combination, and the claimed combination may be directed to a sub combination or variation of a sub combination.

The orientation of various elements may differ according to other exemplary implementations, and such variations are encompassed by the present disclosure. Features of the disclosed implementations can be incorporated into other disclosed implementations.

While various inventive implementations have been described and illustrated herein, a variety of other means and/or structures for performing the function and/or obtaining the results and/or one or more of the advantages described herein are, and each of such variations and/or modifications is, deemed to be within the scope of the inventive implementations described herein. The foregoing implementations are presented by way of example only and that, within the scope of the appended claims and equivalents thereto, inventive implementations may be practiced otherwise than as specifically described and claimed. Inventive implementations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, the technology described herein may be embodied as a method, of which at least one example has been provided. The acts performed as part of the method may be ordered in any suitable way. Accordingly, implementations may be constructed in which acts are performed in an order different than illustrated, which may include performing some acts simultaneously, even though shown as sequential acts in illustrative implementations.

The claims should not be read as limited to the described order or elements unless stated to that effect. It should be understood that various changes in form and detail may be made by one of ordinary skill in the art without departing from the spirit and scope of the appended claims. All implementations that come within the spirit and scope of the following claims and equivalents thereto are claimed.

What is claimed is:

1. A drug delivery device comprising:

a catheter component comprising a stem portion and a branch portion, the catheter component further comprising a pre-defined bend such that the branch portion is angled with respect to the stem portion at an obtuse angle, the catheter component further comprising a dissecting head that is a flattened disc geometry positioned at a distal end of the branch portion, the flattened disc geometry extending radially outward and distally from an outermost diameter of the distal end of the branch portion such that the flattened disc geometry defines a dissecting head diameter that is greater than the outermost diameter of the branch portion, and the catheter component further comprising at least one delivery port positioned in and defined by a portion of the dissecting head;

a drug delivery reservoir coupled to the at least one delivery port through the branch portion and through at least a portion of the stem portion; and a handle portion coupled to the stem portion.

2. The drug delivery device of claim 1, wherein the branch portion is angled with respect to the stem portion at the obtuse angle about two axes.

3. The drug delivery device of claim 1, further comprising a dilation balloon positionable on the branch portion between the pre-defined bend and the dissecting head, the dilation balloon configured to expand around at least a portion of a cylindrical wall of the branch portion; and an outer sheath positionable between the pre-defined bend and the dilation balloon.

4. The drug delivery device of claim 3, wherein the branch portion is configured to retract into and extend from the outer sheath at the obtuse angle.

5. The drug delivery device of claim 4, wherein the dilation balloon is configured to retract into and extend from the outer sheath at the obtuse angle with the branch portion.

6. The drug delivery device of claim 3, wherein the branch portion is configured to extend 2-3 cm past the outer sheath.

7. The drug delivery device of claim 3, wherein the dilation balloon has a length in a range of 1-4 cm.

8. The drug delivery device of claim 3, wherein the dilation balloon has a diameter in a range of 0.1-3 mm.

9. The drug delivery device of claim 3, wherein the branch portion extends upstream and downstream of the dilation balloon such that the dilation balloon is positioned between the dissecting head and a section of the branch portion that is narrower than the dilation balloon in an inflated state, whereby the dilation balloon is configured to form a depot in a target site of a patient, wherein an entry to the depot upon retraction of the branch portion is narrower than a remainder of the depot.

10. The drug delivery device of claim 3, wherein the dissecting head is configured to create a tissue opening having a cross sectional area that is smaller than a cross sectional area of the dilation balloon when inflated.

11. The drug delivery device of claim 3, wherein at least a portion of the branch portion is configured to retract into and extend from the outer sheath at the obtuse angle.

12. The drug delivery device of claim 1, comprising an endoscope positioned adjacent to the pre-defined bend so as to have a field of view of the dissecting head.

13. The drug delivery device of claim 12, wherein the endoscope comprises a camera.

14. The drug delivery device of claim 1, wherein the dissecting head is configured to penetrate a tissue.

15. The drug delivery device of claim 1, wherein the dissecting head comprises a beveled edge.

16. The drug delivery device of claim 1, wherein the dissecting head comprises a cannula having a diameter in a range of 0.25 mm to 3 mm.

17. The drug delivery device of claim 1, further comprising a pump communicably coupled to the drug delivery reservoir and configured to move a drug from the drug delivery reservoir to the at least one delivery port.

18. The drug delivery device of claim 17, wherein the pump comprises a plunger assembly.

19. The drug delivery device of claim 1, wherein the obtuse angle is in a range of 155-170 degrees.

20. The drug delivery device of claim 1, wherein the branch portion has a length in a range of 10-20 cm.

21. The drug delivery device of claim 1, wherein the drug delivery reservoir contains a therapeutically effective amount of a drug for treating a central nervous system disorder.

22. The drug delivery device of claim 1, wherein the dissecting head comprises a cannula or a needle tip.

23. The drug delivery device of claim 1, wherein the dissecting head comprises a dissecting head thickness that is greater at a proximal end of the dissecting head than at a distal end of the dissecting head, and the dissecting head thickness tapers from the proximal end of the dissecting head to the distal end of the dissecting head.

24. A method of drug delivery, the method comprising:

inserting a catheter component of a drug delivery device into a submucosal tissue by penetrating the submucosal tissue via a dissecting head that is a flattened disc geometry positioned at an end of a branch portion of the catheter component extending from a stem portion of the catheter component, the flattened disc geometry extends radially outward and distally from an outermost diameter of the end of the branch portion such that the flattened disc geometry defines a dissecting head diameter that is greater than the outermost diameter of the branch portion, the catheter component comprising a pre-defined bend such that the branch portion is angled with respect to the stem portion at an obtuse angle, and ejecting a drug through a delivery port positioned in and defined by the dissecting head, the drug pumped from a drug reservoir through the stem portion and the branch portion.

* * * * *